United States Patent
Manickam et al.

(10) Patent No.: US 10,359,479 B2
(45) Date of Patent: Jul. 23, 2019

(54) EFFICIENT THERMAL DRIFT COMPENSATION IN DNV VECTOR MAGNETOMETRY

(71) Applicant: Lockheed Martin Corporation, Bethesda, MD (US)

(72) Inventors: Arul Manickam, Mount Laurel, NJ (US); Peter G. Kaup, Marlton, NJ (US)

(73) Assignee: LOCKHEED MARTIN CORPORATION, Bethesda, MD (US)

( * ) Notice: Subject to any disclaimer, the term of this patent is extended or adjusted under 35 U.S.C. 154(b) by 328 days.

(21) Appl. No.: 15/437,038

(22) Filed: Feb. 20, 2017

(65) Prior Publication Data

US 2018/0238989 A1    Aug. 23, 2018

(51) Int. Cl.
*G01R 33/00* (2006.01)
*G01R 33/032* (2006.01)
(Continued)

(52) U.S. Cl.
CPC ......... *G01R 33/0029* (2013.01); *G01N 24/10* (2013.01); *G01R 33/032* (2013.01); *G01R 33/26* (2013.01)

(58) Field of Classification Search
CPC .. G01R 33/0029; G01R 33/032; G01R 33/26; G01N 24/10
See application file for complete search history.

(56) References Cited

U.S. PATENT DOCUMENTS 2,746,027 A    5/1956   Murray
3,359,812 A    12/1967  Everitt
(Continued)

FOREIGN PATENT DOCUMENTS

CN    105738845 A    7/2016
CN    106257602      12/2016
(Continued)

OTHER PUBLICATIONS

U.S. Notice of Allowance dated Oct. 19, 2017, from related U.S. Appl. No. 15/179,957, 5 pages.
(Continued)

*Primary Examiner* — Dixomara Vargas
(74) *Attorney, Agent, or Firm* — Foley & Lardner LLP

(57) ABSTRACT

A system for magnetic detection of an external magnetic field is described. The system includes a nitrogen vacancy (NV) diamond material having a plurality of crystallographic axes, a radio frequency (RF) excitation source, an optical excitation source, an optical detector, and a controller. The RF radio frequency excitation source is configured to provide RF excitations to the NV diamond material to excite electron spin resonances corresponding to the RF excitations. The controller determines the spectral position corresponding to some of the electron spin resonances, determines a measured four-dimensional projection of a magnetic field based on the determined spectral positions of a subset of all of the plurality of spin resonances, where the number of spin resonances in the subset is one half of a total number of the spin resonances, and determines an estimated three-dimensional magnetic field based on the measured four-dimensional magnetic field projections.

28 Claims, 7 Drawing Sheets

(51) Int. Cl.
*G01N 24/10* (2006.01)
*G01R 33/26* (2006.01)

(56) References Cited

U.S. PATENT DOCUMENTS

| | | | |
|---|---|---|---|
| 3,389,333 A | 6/1968 | Wolff et al. |
| 3,490,032 A | 1/1970 | Zurflueh |
| 3,514,723 A | 5/1970 | Cutler |
| 3,518,531 A | 6/1970 | Huggett |
| 3,621,380 A | 11/1971 | Barlow, Jr. |
| 3,745,452 A | 7/1973 | Osburn et al. |
| 3,899,758 A | 8/1975 | Maier et al. |
| 4,025,873 A | 5/1977 | Chilluffo |
| 4,047,805 A | 9/1977 | Sekimura |
| 4,078,247 A | 3/1978 | Albrecht |
| 4,084,215 A | 4/1978 | Willenbrock |
| 4,322,769 A | 3/1982 | Cooper |
| 4,329,173 A | 5/1982 | Culling |
| 4,359,673 A | 11/1982 | Bross et al. |
| 4,368,430 A | 1/1983 | Dale et al. |
| 4,410,926 A | 10/1983 | Hafner et al. |
| 4,437,533 A | 3/1984 | Bierkarre et al. |
| 4,514,083 A | 4/1985 | Fukuoka |
| 4,588,993 A | 5/1986 | Babij et al. |
| 4,636,612 A | 1/1987 | Cullen |
| 4,638,324 A | 1/1987 | Hannan |
| 4,675,522 A | 6/1987 | Arunkumar |
| 4,768,962 A | 9/1988 | Kupfer et al. |
| 4,818,990 A | 4/1989 | Fernandes |
| 4,820,986 A | 4/1989 | Mansfield et al. |
| 4,945,305 A | 7/1990 | Blood |
| 4,958,328 A | 9/1990 | Stubblefield |
| 4,982,158 A | 1/1991 | Nakata et al. |
| 5,019,721 A | 5/1991 | Martens et al. |
| 5,038,103 A | 8/1991 | Scarzello et al. |
| 5,113,136 A | 5/1992 | Hayashi et al. |
| 5,134,369 A | 7/1992 | Lo et al. |
| 5,189,368 A | 2/1993 | Chase |
| 5,200,855 A | 4/1993 | Meredith et al. |
| 5,210,650 A | 5/1993 | O'Brien et al. |
| 5,245,347 A | 9/1993 | Bonta et al. |
| 5,252,912 A | 10/1993 | Merritt et al. |
| 5,301,096 A | 4/1994 | Klontz et al. |
| 5,384,109 A | 1/1995 | Klaveness et al. |
| 5,396,802 A | 3/1995 | Moss |
| 5,420,549 A | 5/1995 | Prestage |
| 5,425,179 A | 6/1995 | Nickel et al. |
| 5,427,915 A | 6/1995 | Ribi et al. |
| 5,548,279 A | 8/1996 | Gaines |
| 5,568,516 A | 10/1996 | Strohallen et al. |
| 5,586,069 A | 12/1996 | Dockser |
| 5,597,762 A | 1/1997 | Popovici et al. |
| 5,638,472 A | 6/1997 | Van Delden |
| 5,694,375 A | 12/1997 | Woodall |
| 5,719,497 A | 2/1998 | Veeser et al. |
| 5,731,996 A | 3/1998 | Gilbert |
| 5,764,061 A | 6/1998 | Asakawa et al. |
| 5,818,352 A | 10/1998 | McClure |
| 5,846,708 A | 12/1998 | Hollis et al. |
| 5,888,925 A | 3/1999 | Smith et al. |
| 5,894,220 A | 4/1999 | Wellstood et al. |
| 5,907,420 A | 5/1999 | Chraplyvy et al. |
| 5,907,907 A | 6/1999 | Ohtomo et al. |
| 5,915,061 A | 6/1999 | Vanoli |
| 5,995,696 A | 11/1999 | Miyagi et al. |
| 6,042,249 A | 3/2000 | Spangenberg |
| 6,057,684 A | 5/2000 | Murakami et al. |
| 6,064,210 A | 5/2000 | Sinclair |
| 6,121,053 A | 9/2000 | Kolber et al. |
| 6,124,862 A | 9/2000 | Boyken et al. |
| 6,130,753 A | 10/2000 | Hopkins et al. |
| 6,144,204 A | 11/2000 | Sementchenko |
| 6,195,231 B1 | 2/2001 | Sedlmayr et al. |
| 6,215,303 B1 | 4/2001 | Weinstock et al. |
| 6,262,574 B1 | 7/2001 | Cho et al. |
| 6,360,173 B1 | 3/2002 | Fullerton |
| 6,398,155 B1 | 6/2002 | Hepner et al. |
| 6,433,944 B1 | 8/2002 | Nagao et al. |
| 6,437,563 B1 | 8/2002 | Simmonds et al. |
| 6,472,651 B1 | 10/2002 | Ukai |
| 6,472,869 B1 | 10/2002 | Upschulte et al. |
| 6,504,365 B2 | 1/2003 | Kitamura |
| 6,518,747 B2 | 2/2003 | Sager et al. |
| 6,542,242 B1 | 4/2003 | Yost et al. |
| 6,621,377 B2 | 9/2003 | Osadchy et al. |
| 6,621,578 B1 | 9/2003 | Mizoguchi |
| 6,636,146 B1 | 10/2003 | Wehoski |
| 6,686,696 B2 | 2/2004 | Mearini et al. |
| 6,690,162 B1 | 2/2004 | Schopohl et al. |
| 6,765,487 B1 | 7/2004 | Holmes et al. |
| 6,788,722 B1 | 9/2004 | Kennedy et al. |
| 6,809,829 B1 | 10/2004 | Takata et al. |
| 7,118,657 B2 | 10/2006 | Golovchenko et al. |
| 7,221,164 B1 | 5/2007 | Barringer |
| 7,277,161 B2 | 10/2007 | Claus |
| 7,305,869 B1 | 12/2007 | Berman et al. |
| 7,307,416 B2 | 12/2007 | Islam et al. |
| 7,342,399 B1 | 3/2008 | Wiegert |
| RE40,343 E | 5/2008 | Anderson |
| 7,400,142 B2 | 7/2008 | Greelish |
| 7,413,011 B1 | 8/2008 | Chee et al. |
| 7,427,525 B2 | 9/2008 | Santori et al. |
| 7,448,548 B1 | 11/2008 | Compton |
| 7,471,805 B2 | 12/2008 | Goldberg |
| 7,474,090 B2 | 1/2009 | Islam et al. |
| 7,543,780 B1 | 6/2009 | Marshall et al. |
| 7,546,000 B2 | 6/2009 | Spillane et al. |
| 7,570,050 B2 | 8/2009 | Sugiura |
| 7,608,820 B1 | 10/2009 | Berman et al. |
| 7,705,599 B2 | 4/2010 | Strack et al. |
| 7,741,936 B1 | 6/2010 | Weller et al. |
| 7,805,030 B2 | 9/2010 | Bratkovski et al. |
| 7,868,702 B2 | 1/2011 | Ohnishi |
| 7,889,484 B2 | 2/2011 | Choi |
| 7,916,489 B2 | 3/2011 | Okuya |
| 7,932,718 B1 | 4/2011 | Wiegert |
| 7,983,812 B2 | 7/2011 | Potter |
| 8,022,693 B2 | 9/2011 | Meyersweissflog |
| 8,120,351 B2 | 2/2012 | Rettig et al. |
| 8,120,355 B1 | 2/2012 | Stetson |
| 8,124,296 B1 | 2/2012 | Fischel |
| 8,138,756 B2 | 3/2012 | Barclay et al. |
| 8,193,808 B2 | 6/2012 | Fu et al. |
| 8,294,306 B2 | 10/2012 | Kumar et al. |
| 8,310,251 B2 | 11/2012 | Orazem |
| 8,311,767 B1 | 11/2012 | Stetson |
| 8,334,690 B2 | 12/2012 | Kitching et al. |
| 8,415,640 B2 | 4/2013 | Babinec et al. |
| 8,471,137 B2 | 6/2013 | Adair et al. |
| 8,480,653 B2 | 7/2013 | Birchard et al. |
| 8,525,516 B2 | 9/2013 | Le Prado et al. |
| 8,547,090 B2 | 10/2013 | Lukin et al. |
| 8,574,536 B2 | 11/2013 | Boudou et al. |
| 8,575,929 B1 | 11/2013 | Wiegert |
| 8,686,377 B2 | 4/2014 | Twitchen et al. |
| 8,704,546 B2 | 4/2014 | Konstantinov |
| 8,758,509 B2 | 6/2014 | Twitchen et al. |
| 8,803,513 B2 | 8/2014 | Hosek et al. |
| 8,854,839 B2 | 10/2014 | Cheng et al. |
| 8,885,301 B1 | 11/2014 | Heidmann |
| 8,913,900 B2 | 12/2014 | Lukin et al. |
| 8,933,594 B2 | 1/2015 | Kurs |
| 8,947,080 B2 | 2/2015 | Lukin et al. |
| 8,963,488 B2 | 2/2015 | Campanella et al. |
| 9,103,873 B1 | 8/2015 | Martens et al. |
| 9,157,859 B2 | 10/2015 | Walsworth et al. |
| 9,245,551 B2 | 1/2016 | El Hallak et al. |
| 9,249,526 B2 | 2/2016 | Twitchen et al. |
| 9,270,387 B2 | 2/2016 | Wolfe et al. |
| 9,291,508 B1 | 3/2016 | Biedermann et al. |
| 9,317,811 B2 | 4/2016 | Scarsbrook |
| 9,369,182 B2 | 6/2016 | Kurs et al. |
| 9,442,205 B2 | 9/2016 | Geiser et al. |
| 9,541,610 B2 | 1/2017 | Kaup et al. |

(56) References Cited

U.S. PATENT DOCUMENTS

| | | |
|---|---|---|
| 9,551,763 B1 | 1/2017 | Hahn et al. |
| 9,557,391 B2 | 1/2017 | Egan et al. |
| 9,570,793 B2 | 2/2017 | Borodulin |
| 9,590,601 B2 | 3/2017 | Krause et al. |
| 9,614,589 B1 | 4/2017 | Russo et al. |
| 9,632,045 B2* | 4/2017 | Englund ............ G01N 24/006 |
| 9,645,223 B2 | 5/2017 | Megdal et al. |
| 9,680,338 B2 | 6/2017 | Malpas et al. |
| 9,689,679 B2 | 6/2017 | Budker et al. |
| 9,720,055 B1 | 8/2017 | Hahn et al. |
| 9,778,329 B2 | 10/2017 | Heidmann |
| 9,779,769 B2 | 10/2017 | Heidmann |
| 9,891,297 B2* | 2/2018 | Sushkov ............... G01N 24/12 |
| 2002/0144093 A1 | 10/2002 | Inoue et al. |
| 2002/0167306 A1 | 11/2002 | Zalunardo et al. |
| 2003/0058346 A1 | 3/2003 | Bechtel et al. |
| 2003/0076229 A1 | 4/2003 | Blanpain et al. |
| 2003/0094942 A1 | 5/2003 | Friend et al. |
| 2003/0098455 A1 | 5/2003 | Amin et al. |
| 2003/0235136 A1 | 12/2003 | Akselrod et al. |
| 2004/0013180 A1 | 1/2004 | Giannakis et al. |
| 2004/0022179 A1 | 2/2004 | Giannakis et al. |
| 2004/0042150 A1 | 3/2004 | Swinbanks et al. |
| 2004/0081033 A1 | 4/2004 | Arieli et al. |
| 2004/0095133 A1 | 5/2004 | Nikitin et al. |
| 2004/0109328 A1 | 6/2004 | Dahl et al. |
| 2004/0247145 A1 | 12/2004 | Luo et al. |
| 2005/0031840 A1 | 2/2005 | Swift et al. |
| 2005/0068249 A1 | 3/2005 | Frederick Du Toit et al. |
| 2005/0099177 A1 | 5/2005 | Greelish |
| 2005/0112594 A1 | 5/2005 | Grossman |
| 2005/0126905 A1 | 6/2005 | Golovchenko et al. |
| 2005/0130601 A1 | 6/2005 | Palermo et al. |
| 2005/0134257 A1 | 6/2005 | Etherington et al. |
| 2005/0138330 A1 | 6/2005 | Owens et al. |
| 2005/0146327 A1 | 7/2005 | Jakab |
| 2006/0012385 A1 | 1/2006 | Tsao et al. |
| 2006/0054789 A1 | 3/2006 | Miyamoto et al. |
| 2006/0055584 A1 | 3/2006 | Waite et al. |
| 2006/0062084 A1 | 3/2006 | Drew |
| 2006/0071709 A1 | 4/2006 | Maloberti et al. |
| 2006/0245078 A1 | 11/2006 | Kawamura |
| 2006/0247847 A1 | 11/2006 | Carter et al. |
| 2006/0255801 A1 | 11/2006 | Ikeda |
| 2006/0291771 A1 | 12/2006 | Braunisch et al. |
| 2007/0004371 A1 | 1/2007 | Okanobu |
| 2007/0120563 A1 | 5/2007 | Kawabata et al. |
| 2007/0247147 A1 | 10/2007 | Xiang et al. |
| 2007/0273877 A1 | 11/2007 | Kawano et al. |
| 2008/0016677 A1 | 1/2008 | Creighton, IV |
| 2008/0048640 A1 | 2/2008 | Hull et al. |
| 2008/0078233 A1 | 4/2008 | Larson et al. |
| 2008/0089367 A1 | 4/2008 | Srinivasan et al. |
| 2008/0204004 A1 | 8/2008 | Anderson |
| 2008/0217516 A1 | 9/2008 | Suzuki et al. |
| 2008/0239265 A1 | 10/2008 | Den Boef |
| 2008/0253264 A1 | 10/2008 | Nagatomi et al. |
| 2008/0265895 A1 | 10/2008 | Strack et al. |
| 2008/0266050 A1 | 10/2008 | Crouse et al. |
| 2008/0279047 A1 | 11/2008 | An et al. |
| 2008/0299904 A1 | 12/2008 | Yi et al. |
| 2009/0001979 A1 | 1/2009 | Kawabata |
| 2009/0015262 A1 | 1/2009 | Strack et al. |
| 2009/0042592 A1 | 2/2009 | Cho et al. |
| 2009/0058697 A1 | 3/2009 | Aas et al. |
| 2009/0060790 A1 | 3/2009 | Okaguchi et al. |
| 2009/0079417 A1 | 3/2009 | Mort et al. |
| 2009/0079426 A1 | 3/2009 | Anderson |
| 2009/0132100 A1 | 5/2009 | Shibata |
| 2009/0157331 A1 | 6/2009 | Van Netten |
| 2009/0161264 A1 | 6/2009 | Meyersweissflog |
| 2009/0195244 A1 | 8/2009 | Mouget et al. |
| 2009/0222208 A1 | 9/2009 | Speck |
| 2009/0243616 A1 | 10/2009 | Loehken et al. |
| 2009/0244857 A1 | 10/2009 | Tanaka |
| 2009/0277702 A1 | 11/2009 | Kanada et al. |
| 2009/0310650 A1 | 12/2009 | Chester et al. |
| 2010/0004802 A1 | 1/2010 | Bodin et al. |
| 2010/0015438 A1 | 1/2010 | Williams et al. |
| 2010/0015918 A1 | 1/2010 | Liu et al. |
| 2010/0045269 A1 | 2/2010 | Lafranchise et al. |
| 2010/0071904 A1 | 3/2010 | Burns et al. |
| 2010/0102809 A1 | 4/2010 | May |
| 2010/0102820 A1 | 4/2010 | Martinez et al. |
| 2010/0134922 A1 | 6/2010 | Yamada et al. |
| 2010/0157305 A1 | 6/2010 | Henderson |
| 2010/0188081 A1 | 7/2010 | Lammegger |
| 2010/0237149 A1 | 9/2010 | Olmstead |
| 2010/0271016 A1 | 10/2010 | Barclay et al. |
| 2010/0271032 A1 | 10/2010 | Helwig |
| 2010/0277121 A1 | 11/2010 | Hall et al. |
| 2010/0308813 A1 | 12/2010 | Lukin et al. |
| 2010/0315079 A1 | 12/2010 | Lukin et al. |
| 2010/0321117 A1 | 12/2010 | Gan |
| 2010/0326042 A1 | 12/2010 | McLean et al. |
| 2011/0031969 A1 | 2/2011 | Kitching et al. |
| 2011/0034393 A1 | 2/2011 | Justen et al. |
| 2011/0059704 A1 | 3/2011 | Norimatsu et al. |
| 2011/0062957 A1 | 3/2011 | Fu et al. |
| 2011/0062967 A1 | 3/2011 | Mohaupt |
| 2011/0066379 A1 | 3/2011 | Mes |
| 2011/0120890 A1 | 5/2011 | MacPherson et al. |
| 2011/0127999 A1 | 6/2011 | Lott et al. |
| 2011/0165862 A1 | 7/2011 | Yu et al. |
| 2011/0175604 A1 | 7/2011 | Polzer et al. |
| 2011/0176563 A1 | 7/2011 | Friel et al. |
| 2011/0243267 A1 | 10/2011 | Won et al. |
| 2011/0270078 A1 | 11/2011 | Wagenaar et al. |
| 2011/0279120 A1 | 11/2011 | Sudow et al. |
| 2011/0315988 A1 | 12/2011 | Yu et al. |
| 2012/0016538 A1 | 1/2012 | Waite et al. |
| 2012/0019242 A1 | 1/2012 | Hollenberg et al. |
| 2012/0037803 A1 | 2/2012 | Strickland |
| 2012/0044014 A1 | 2/2012 | Stratakos et al. |
| 2012/0051996 A1 | 3/2012 | Scarsbrook et al. |
| 2012/0063505 A1 | 3/2012 | Okamura et al. |
| 2012/0087449 A1 | 4/2012 | Ling et al. |
| 2012/0089299 A1 | 4/2012 | Breed |
| 2012/0140219 A1 | 6/2012 | Cleary |
| 2012/0181020 A1 | 7/2012 | Barron et al. |
| 2012/0194068 A1 | 8/2012 | Cheng et al. |
| 2012/0203086 A1 | 8/2012 | Rorabaugh et al. |
| 2012/0232838 A1 | 9/2012 | Kemppi et al. |
| 2012/0235633 A1 | 9/2012 | Kesler et al. |
| 2012/0235634 A1 | 9/2012 | Hall et al. |
| 2012/0245885 A1 | 9/2012 | Kimishima |
| 2012/0257683 A1 | 10/2012 | Schwager et al. |
| 2012/0281843 A1 | 11/2012 | Christensen et al. |
| 2012/0326793 A1 | 12/2012 | Gan |
| 2013/0043863 A1 | 2/2013 | Ausserlechner et al. |
| 2013/0070252 A1 | 3/2013 | Feth |
| 2013/0093424 A1 | 4/2013 | Blank et al. |
| 2013/0107253 A1 | 5/2013 | Santori |
| 2013/0127518 A1 | 5/2013 | Nakao |
| 2013/0179074 A1 | 7/2013 | Haverinen |
| 2013/0215712 A1 | 8/2013 | Geiser et al. |
| 2013/0223805 A1 | 8/2013 | Ouyang et al. |
| 2013/0265042 A1 | 10/2013 | Kawabata et al. |
| 2013/0265782 A1 | 10/2013 | Barrena et al. |
| 2013/0270991 A1 | 10/2013 | Twitchen et al. |
| 2013/0279319 A1 | 10/2013 | Matozaki et al. |
| 2013/0292472 A1 | 11/2013 | Guha |
| 2014/0012505 A1 | 1/2014 | Smith et al. |
| 2014/0015522 A1 | 1/2014 | Widmer et al. |
| 2014/0037932 A1 | 2/2014 | Twitchen et al. |
| 2014/0044208 A1 | 2/2014 | Woodsum |
| 2014/0061510 A1 | 3/2014 | Twitchen et al. |
| 2014/0070622 A1 | 3/2014 | Keeling et al. |
| 2014/0072008 A1 | 3/2014 | Faraon et al. |
| 2014/0077231 A1 | 3/2014 | Twitchen et al. |
| 2014/0081592 A1 | 3/2014 | Bellusci et al. |
| 2014/0104008 A1 | 4/2014 | Gan |
| 2014/0126334 A1 | 5/2014 | Megdal et al. |
| 2014/0139322 A1 | 5/2014 | Wang et al. |

(56) References Cited

U.S. PATENT DOCUMENTS

| | | |
|---|---|---|
| 2014/0153363 A1 | 6/2014 | Juhasz et al. |
| 2014/0154792 A1 | 6/2014 | Moynihan et al. |
| 2014/0159652 A1 | 6/2014 | Hall et al. |
| 2014/0166904 A1 | 6/2014 | Walsworth et al. |
| 2014/0167759 A1 | 6/2014 | Pines et al. |
| 2014/0168174 A1 | 6/2014 | Idzik et al. |
| 2014/0180627 A1 | 6/2014 | Naguib et al. |
| 2014/0191139 A1 | 7/2014 | Englund |
| 2014/0191752 A1 | 7/2014 | Walsworth et al. |
| 2014/0197831 A1 | 7/2014 | Walsworth |
| 2014/0198463 A1 | 7/2014 | Klein |
| 2014/0210473 A1 | 7/2014 | Campbell et al. |
| 2014/0215985 A1 | 8/2014 | Pollklas |
| 2014/0225606 A1 | 8/2014 | Endo et al. |
| 2014/0247094 A1 | 9/2014 | Englund et al. |
| 2014/0264723 A1 | 9/2014 | Liang et al. |
| 2014/0265555 A1 | 9/2014 | Hall et al. |
| 2014/0272119 A1 | 9/2014 | Kushalappa et al. |
| 2014/0273826 A1 | 9/2014 | Want et al. |
| 2014/0291490 A1 | 10/2014 | Hanson et al. |
| 2014/0297067 A1 | 10/2014 | Malay |
| 2014/0306707 A1 | 10/2014 | Walsworth et al. |
| 2014/0327439 A1 | 11/2014 | Cappellaro et al. |
| 2014/0335339 A1 | 11/2014 | Dhillon et al. |
| 2014/0340085 A1 | 11/2014 | Cappellaro et al. |
| 2014/0368191 A1 | 12/2014 | Goroshevskiy et al. |
| 2015/0001422 A1 | 1/2015 | Englund et al. |
| 2015/0009746 A1 | 1/2015 | Kucsko et al. |
| 2015/0015247 A1 | 1/2015 | Goodwill et al. |
| 2015/0018018 A1 | 1/2015 | Shen et al. |
| 2015/0022404 A1 | 1/2015 | Chen et al. |
| 2015/0048822 A1 | 2/2015 | Walsworth et al. |
| 2015/0054355 A1 | 2/2015 | Ben-Shalom et al. |
| 2015/0061590 A1 | 3/2015 | Widmer et al. |
| 2015/0061670 A1 | 3/2015 | Fordham et al. |
| 2015/0090033 A1 | 4/2015 | Budker et al. |
| 2015/0128431 A1 | 5/2015 | Kuo |
| 2015/0137793 A1 | 5/2015 | Englund et al. |
| 2015/0153151 A1 | 6/2015 | Kochanski |
| 2015/0192532 A1 | 7/2015 | Clevenson et al. |
| 2015/0192596 A1 | 7/2015 | Englund et al. |
| 2015/0225052 A1 | 8/2015 | Cordell |
| 2015/0235661 A1 | 8/2015 | Heidmann |
| 2015/0253355 A1 | 9/2015 | Grinolds et al. |
| 2015/0268373 A1 | 9/2015 | Meyer |
| 2015/0269957 A1 | 9/2015 | El Hallak et al. |
| 2015/0276897 A1 | 10/2015 | Leussler et al. |
| 2015/0288352 A1 | 10/2015 | Krause et al. |
| 2015/0299894 A1 | 10/2015 | Markham et al. |
| 2015/0303333 A1 | 10/2015 | Yu et al. |
| 2015/0314870 A1 | 11/2015 | Davies |
| 2015/0326030 A1 | 11/2015 | Malpas et al. |
| 2015/0326410 A1 | 11/2015 | Krause et al. |
| 2015/0354985 A1 | 12/2015 | Judkins et al. |
| 2015/0358026 A1 | 12/2015 | Gan |
| 2015/0374250 A1 | 12/2015 | Hatano et al. |
| 2015/0377865 A1 | 12/2015 | Acosta et al. |
| 2015/0377987 A1 | 12/2015 | Menon et al. |
| 2016/0018269 A1 | 1/2016 | Maurer et al. |
| 2016/0031339 A1 | 2/2016 | Geo |
| 2016/0036529 A1 | 2/2016 | Griffith et al. |
| 2016/0052789 A1 | 2/2016 | Gaathon et al. |
| 2016/0054402 A1 | 2/2016 | Meriles |
| 2016/0061914 A1 | 3/2016 | Jelezko |
| 2016/0071532 A9 | 3/2016 | Heidmann |
| 2016/0077167 A1 | 3/2016 | Heidmann |
| 2016/0097702 A1 | 4/2016 | Zhao et al. |
| 2016/0113507 A1 | 4/2016 | Reza et al. |
| 2016/0131723 A1 | 5/2016 | Nagasaka |
| 2016/0139048 A1 | 5/2016 | Heidmann |
| 2016/0146904 A1 | 5/2016 | Stetson, Jr. et al. |
| 2016/0161429 A1* | 6/2016 | Englund ............ G01N 24/006 324/304 |
| 2016/0161583 A1 | 6/2016 | Meriles et al. |
| 2016/0174867 A1 | 6/2016 | Hatano |
| 2016/0214714 A1 | 7/2016 | Sekelsky |
| 2016/0216304 A1 | 7/2016 | Sekelsky |
| 2016/0216340 A1 | 7/2016 | Egan et al. |
| 2016/0216341 A1 | 7/2016 | Boesch et al. |
| 2016/0221441 A1 | 8/2016 | Hall et al. |
| 2016/0223621 A1 | 8/2016 | Kaup et al. |
| 2016/0231394 A1 | 8/2016 | Manickam et al. |
| 2016/0266220 A1 | 9/2016 | Sushkov et al. |
| 2016/0282427 A1 | 9/2016 | Heidmann |
| 2016/0291191 A1 | 10/2016 | Fukushima et al. |
| 2016/0313408 A1 | 10/2016 | Hatano et al. |
| 2016/0348277 A1 | 12/2016 | Markham et al. |
| 2016/0356863 A1 | 12/2016 | Boesch et al. |
| 2017/0010214 A1 | 1/2017 | Osawa et al. |
| 2017/0010334 A1 | 1/2017 | Krause et al. |
| 2017/0010338 A1 | 1/2017 | Bayat et al. |
| 2017/0010594 A1 | 1/2017 | Kottapalli et al. |
| 2017/0023487 A1 | 1/2017 | Boesch |
| 2017/0030982 A1 | 2/2017 | Jeske et al. |
| 2017/0038314 A1 | 2/2017 | Suyama et al. |
| 2017/0038411 A1 | 2/2017 | Yacobi et al. |
| 2017/0068012 A1 | 3/2017 | Fisk |
| 2017/0074660 A1 | 3/2017 | Gann et al. |
| 2017/0075020 A1 | 3/2017 | Gann et al. |
| 2017/0075205 A1 | 3/2017 | Kriman et al. |
| 2017/0077665 A1 | 3/2017 | Liu et al. |
| 2017/0104426 A1 | 4/2017 | Mills |
| 2017/0138735 A1 | 5/2017 | Cappellaro et al. |
| 2017/0139017 A1 | 5/2017 | Egan et al. |
| 2017/0146615 A1 | 5/2017 | Wolf et al. |
| 2017/0199156 A1 | 7/2017 | Villani et al. |
| 2017/0205526 A1 | 7/2017 | Meyer |
| 2017/0207823 A1 | 7/2017 | Russo et al. |
| 2017/0211947 A1 | 7/2017 | Fisk |
| 2017/0212046 A1 | 7/2017 | Cammerata |
| 2017/0212177 A1 | 7/2017 | Coar et al. |
| 2017/0212178 A1 | 7/2017 | Hahn et al. |
| 2017/0212179 A1 | 7/2017 | Hahn et al. |
| 2017/0212180 A1 | 7/2017 | Hahn et al. |
| 2017/0212181 A1 | 7/2017 | Coar et al. |
| 2017/0212182 A1 | 7/2017 | Hahn et al. |
| 2017/0212183 A1 | 7/2017 | Egan et al. |
| 2017/0212184 A1 | 7/2017 | Coar et al. |
| 2017/0212185 A1 | 7/2017 | Hahn et al. |
| 2017/0212186 A1 | 7/2017 | Hahn et al. |
| 2017/0212187 A1 | 7/2017 | Hahn et al. |
| 2017/0212190 A1 | 7/2017 | Reynolds et al. |
| 2017/0212258 A1 | 7/2017 | Fisk |
| 2017/0261629 A1 | 9/2017 | Gunnarsson et al. |
| 2017/0343617 A1 | 11/2017 | Manickam et al. |
| 2017/0343619 A1 | 11/2017 | Manickam et al. |
| 2017/0343621 A1 | 11/2017 | Hahn et al. |
| 2017/0343695 A1* | 11/2017 | Stetson ................. G01V 3/101 |
| 2018/0136291 A1 | 5/2018 | Pham et al. |
| 2018/0275209 A1 | 9/2018 | Mandeville et al. |
| 2018/0275212 A1 | 9/2018 | Hahn et al. |
| 2019/0018085 A1* | 1/2019 | Wu ........................ G01R 33/26 |

FOREIGN PATENT DOCUMENTS

| | | |
|---|---|---|
| DE | 69608006 T2 | 2/2001 |
| DE | 19600241 C2 | 8/2002 |
| DE | 10228536 A1 | 1/2003 |
| EP | 0 161 940 B1 | 12/1990 |
| EP | 0 718 642 | 6/1996 |
| EP | 0 726 458 | 8/1996 |
| EP | 1 505 627 | 2/2005 |
| EP | 1 685 597 | 8/2006 |
| EP | 1 990 313 | 11/2008 |
| EP | 2 163 392 | 3/2010 |
| EP | 2 495 166 A1 | 9/2012 |
| EP | 2 587 232 A1 | 5/2013 |
| EP | 2 705 179 | 3/2014 |
| EP | 2 707 523 | 3/2014 |
| EP | 2 745 360 | 6/2014 |
| EP | 2 769 417 | 8/2014 |
| EP | 2 790 031 | 10/2014 |
| EP | 2 837 930 A1 | 2/2015 |
| EP | 2 907 792 | 8/2015 |

(56) References Cited

FOREIGN PATENT DOCUMENTS

| | | |
|---|---|---|
| GB | 2 423 366 A | 8/2006 |
| GB | 2 433 737 | 7/2007 |
| GB | 2 482 596 | 2/2012 |
| GB | 2 483 767 | 3/2012 |
| GB | 2 486 794 | 6/2012 |
| GB | 2 490 589 | 11/2012 |
| GB | 2 491 936 | 12/2012 |
| GB | 2 493 236 | 1/2013 |
| GB | 2 495 632 A | 4/2013 |
| GB | 2 497 660 | 6/2013 |
| GB | 2 510 053 A | 7/2014 |
| GB | 2 515 226 | 12/2014 |
| GB | 2 522 309 | 7/2015 |
| GB | 2 526 639 | 12/2015 |
| JP | 3782147 B2 | 6/2006 |
| JP | 4800896 B2 | 10/2011 |
| JP | 2012-103171 | 5/2012 |
| JP | 2012-110489 | 6/2012 |
| JP | 2012-121748 | 6/2012 |
| JP | 2013-028497 | 2/2013 |
| JP | 5476206 B2 | 4/2014 |
| JP | 5522606 B2 | 6/2014 |
| JP | 5536056 B2 | 7/2014 |
| JP | 5601183 B2 | 10/2014 |
| JP | 2014-215985 | 11/2014 |
| JP | 2014-216596 | 11/2014 |
| JP | 2015-518562 A | 7/2015 |
| JP | 5764059 B2 | 8/2015 |
| JP | 2015-167176 | 9/2015 |
| JP | 2015-529328 | 10/2015 |
| JP | 5828036 B2 | 12/2015 |
| JP | 5831947 B2 | 12/2015 |
| WO | WO-87/04028 A1 | 7/1987 |
| WO | WO-88/04032 A1 | 6/1988 |
| WO | WO-95/33972 A1 | 12/1995 |
| WO | WO-2009/073736 | 6/2009 |
| WO | WO-2011/046403 A2 | 4/2011 |
| WO | WO-2011/153339 A1 | 12/2011 |
| WO | WO-2012/016977 A2 | 2/2012 |
| WO | WO-2012/084750 | 6/2012 |
| WO | WO-2013/027074 | 2/2013 |
| WO | WO-2013/059404 A1 | 4/2013 |
| WO | WO-2013/066446 A1 | 5/2013 |
| WO | WO-2013/066448 | 5/2013 |
| WO | WO-2013/093136 A1 | 6/2013 |
| WO | WO-2013/188732 A1 | 12/2013 |
| WO | WO-2013/190329 A1 | 12/2013 |
| WO | WO-2014/011286 A2 | 1/2014 |
| WO | WO-2014/099110 A2 | 6/2014 |
| WO | WO-2014/135544 A1 | 9/2014 |
| WO | WO-2014/135547 A1 | 9/2014 |
| WO | WO-2014/166883 A1 | 10/2014 |
| WO | WO-2014/210486 A1 | 12/2014 |
| WO | WO-2015/015172 A1 | 2/2015 |
| WO | WO-2015/142945 | 9/2015 |
| WO | WO-2015/157110 A1 | 10/2015 |
| WO | WO-2015/157290 A1 | 10/2015 |
| WO | WO-2015/158383 A1 | 10/2015 |
| WO | WO-2015/193156 A1 | 12/2015 |
| WO | WO-2016/075226 A1 | 5/2016 |
| WO | WO-2016/118756 A1 | 7/2016 |
| WO | WO-2016/118791 A1 | 7/2016 |
| WO | WO-2016/122965 A1 | 8/2016 |
| WO | WO-2016/122966 A1 | 8/2016 |
| WO | WO-2016/126435 A1 | 8/2016 |
| WO | WO-2016/126436 A1 | 8/2016 |
| WO | PCT/US2016/066566 | 12/2016 |
| WO | PCT/US2016/068320 | 12/2016 |
| WO | PCT/US2016/068344 | 12/2016 |
| WO | PCT/US2016/068366 | 12/2016 |
| WO | WO-2016/190909 A2 | 12/2016 |
| WO | WO-2017/007513 A1 | 1/2017 |
| WO | WO-2017/007514 A1 | 1/2017 |
| WO | WO-2017/014807 A1 | 1/2017 |
| WO | PCT/US2017/017321 | 2/2017 |
| WO | PCT/US2017/018099 | 2/2017 |
| WO | PCT/US2017/018701 | 2/2017 |
| WO | PCT/US2017/018709 | 2/2017 |
| WO | PCT/US2017/019411 | 2/2017 |
| WO | PCT/US2017/021593 | 3/2017 |
| WO | PCT/US2017/021811 | 3/2017 |
| WO | PCT/US2017/022118 | 3/2017 |
| WO | PCT/US2017/022279 | 3/2017 |
| WO | PCT/US2017/024165 | 3/2017 |
| WO | PCT/US2017/024167 | 3/2017 |
| WO | PCT/US2017/024168 | 3/2017 |
| WO | PCT/US2017/024169 | 3/2017 |
| WO | PCT/US2017/024171 | 3/2017 |
| WO | PCT/US2017/024172 | 3/2017 |
| WO | PCT/US2017/024173 | 3/2017 |
| WO | PCT/US2017/024174 | 3/2017 |
| WO | PCT/US2017/024175 | 3/2017 |
| WO | PCT/US2017/024177 | 3/2017 |
| WO | PCT/US2017/024179 | 3/2017 |
| WO | PCT/US2017/024180 | 3/2017 |
| WO | PCT/US2017/024181 | 3/2017 |
| WO | PCT/US2017/024182 | 3/2017 |
| WO | WO-2017/039747 A1 | 3/2017 |
| WO | PCT/US2017/035315 | 5/2017 |
| WO | WO-2017/095454 A1 | 6/2017 |
| WO | WO-2017/127079 A1 | 7/2017 |
| WO | WO-2017/127080 A1 | 7/2017 |
| WO | WO-2017/127081 A1 | 7/2017 |
| WO | WO-2017/127085 A1 | 7/2017 |
| WO | WO-2017/127090 A1 | 7/2017 |
| WO | WO-2017/127091 A1 | 7/2017 |
| WO | WO-2017/127093 A1 | 7/2017 |
| WO | WO-2017/127094 A1 | 7/2017 |
| WO | WO-2017/127095 A1 | 7/2017 |
| WO | WO-2017/127096 A1 | 7/2017 |
| WO | WO-2017/127097 A1 | 7/2017 |
| WO | WO-2017/127098 A1 | 7/2017 |

OTHER PUBLICATIONS

U.S. Notice of Allowance dated Oct. 23, 2017, from related U.S. Appl. No. 15/003,797, 6 pages.

U.S. Office Action dated Nov. 24, 2017, from related U.S. Appl. No. 15/003,145, 14 pages.

U.S. Office Action dated Nov. 27, 2017, from related U.S. Appl. No. 15/468,386, 28 pages.

"'Diamond Sensors, Detectors, and Quantum Devices' in Patent Application Approval Process," Chemicals & Chemistry, pp. 1-6, (Feb. 28, 2014), 6 pages.

"Findings from University of Stuttgart in physics reported," Science Letter, (Jul. 7, 2009), 2 pages.

"New Findings on Nitrogen from Ecole Normale Superieure Summarized (Magnetic imaging with an ensemble of nitrogen vacancy-centers in diamond)," Physics Week, pp. 1-2, (Jul. 21, 2015), 2 pages.

"Patent Issued for Diamond Sensors, Detectors, and Quantum Devices (U.S. Pat. No. 9,249,526)," Journal of Engineering, pp. 1-5 (Feb. 15, 2016), 5 pages.

"Researchers Submit Patent Application, 'Diamond Sensors, Detectors, and Quantum Devices', for Approval," Chemicals & Chemistry, pp. 1-7, (Apr. 11, 2014), 7 pages.

Acosta et al., "Broadband magnetometry by infrared-absorption detection of nitrogen-vacancy ensembles in diamond," Appl. Phys. Letters 97: 174104 (Oct. 29, 2010), 4 pages.

Acosta et al., "Diamonds with a high density of nitrogen-vacancy centers for magnetometry applications," Physical Review B 80(115202): 1-15 (Sep. 9, 2009), 15 pages.

Acosta et al., "Nitrogen-vacancy centers: physics and applications," MRS Bulletin 38(2): 127-130 (Feb. 2013), 4 pages.

Acosta, "Optical Magnetometry with Nitrogen-Vacancy Centers in Diamond," University of California Berkeley, (Spring 2011), 118 pages.

Aiello et al., "Composite-pulse magnetometry with a solid-state quantum sensor," Nature Communications 4(1419): 1-6 (Jan. 29, 2013), 6 pages.

(56) References Cited

OTHER PUBLICATIONS

Alam, "Solid-state 13C magic angle spinning NMR spectroscopy characterization of particle size structural variations in synthetic nanodiamonds," Materials Chemistry and Physics 85(2-3): 310-315 (Jun. 15, 2004), 6 pages.

Albrecht et al., "Coupling of nitrogen vacancy centres in nanodiamonds by means of phonons," New Journal of Physics 15(083014): 1-26 (Aug. 6, 2013), 27 pages.

Appel et al., "Nanoscale microwave imaging with a single electron spin in diamond," New Journal of Physics 17(112001): 1-6 (Nov. 3, 2015), 7 pages.

Arai et al., "Fourier magnetic imaging with nanoscale resolution and compressed sensing speed-up using electronic spins in diamond," Nature Nanotechnology 10: 859-864 (Aug. 10, 2015), 7 pages.

Aslam et al., "Single spin optically detected magnetic resonance with 60-90 GHz (E-band) microwave resonators," Review of Scientific Instruments 86(064704): 1-8 (Jun. 22, 2015), 9 pages.

Awschalom et al., "Diamond age of spintronics," Scientific American 297: 84-91 (Oct. 2007), 8 pages.

Babamoradi et al., "Correlation between entanglement and spin density in nitrogen-vacancy center of diamond," European Physical Journal D 65: 597-603 (Dec. 1, 2011), 7 pages.

Babunts et al., "Diagnostics of NV defect structure orientation in diamond using optically detected magnetic resonance with a modulated magnetic field," Technical Physics Letters 41(6): 583-586 (Jun. 2015; first published online Jul. 14, 2015), 4 pages.

Babunts et al., "Temperature-scanned magnetic resonance and the evidence of two-way transfer of a nitrogen nuclear spin hyperfine interaction in coupled NV-N pairs in diamond," JETP Letters 95(8): 429-432 (Jun. 27, 2012), 4 pages.

Bagguley et al., "Zeeman effect of acceptor states in semiconducting diamond," Journal of the Physical Society of Japan 21(Supplement): 244-248 (1966), 7 pages.

Balasubramanian et al., "Nanoscale imaging magnetometry with diamond spins under ambient conditions," Nature 455: 648-651 (Oct. 2, 2008), 5 pages.

Balmer et al., "Chemical Vapour deposition synthetic diamond: materials technology and applications," J. of Physics: Condensed Matter 21(36): 1-51 (Aug. 19, 2009), 51 pages.

Baranov et al., "Enormously High Concentrations of Fluorescent Nitrogen-Vacancy Centers Fabricated by Sintering of Detonation Nanodiamonds," Small 7(11): 1533-1537 (Jun. 6, 2011; first published online Apr. 26, 2011), 5 pages.

Barfuss et al., "Strong mechanical driving of a single electron spin," Nature Physics 11: 820-824 (Aug. 3, 2015), 6 pages.

Barry et al., "Optical magnetic detection of single-neuron action potentials using quantum defects in diamond," as submitted to Quantum Physics on Feb. 2, 2016, 23 pages.

Bennett et al., "CVD Diamond for High Power Laser Applications," SPIE 8603, High-Power Laser Materials Processing: Lasers, Beam Delivery, Diagnostics, and Applications II, 860307 (Feb. 22, 2013), 10 pages.

Berman & Chernobrod, "Single-spin microscope with sub-nanoscale resolution based on optically detected magnetic resonance," SPIE 7608, Quantum Sensing and Nanophotonic Devices VII, 76080Y (Jan. 23, 2010), 4 pages.

Berman et al. "Measurement of single electron and nuclear spin states based on optically detected magnetic resonance," J. Physics: Conf. Series 38: 167-170 (2006), 5 pages.

Blakley et al., "Room-temperature magnetic gradiometry with fiber-coupled nitrogen-vacancy centers in diamond," Optics Letters 40(16): 3727-3730 (Aug. 5, 2015), 4 pages.

Bourgeois, et al., "Photoelectric detection of electron spin resonance of nitrogen-vacancy centres in diamond," Nature Communications 6(8577): 1-8 (Oct. 21, 2015), 8 pages.

Brenneis, et al. "Ultrafast electronic readout of diamond nitrogen-vacancy centres coupled to graphene." Nature nanotechnology 10.2 (2015): 135-139.

Bucher et al, "High Resolution Magnetic Resonance Spectroscopy Using Solid-State Spins", May 25, 2017, downloaded from https://arxiv.org/ (arXiv.org > quant-ph > arXiv:1705.08887) on May 25, 2017, pp. 1-24.

Budker & Kimball, "Optical Magnetometry," Cambridge Press, (2013), 11 pages.

Budker & Romalis, "Optical Magnetometry," Nature Physics 3: 227-243 (Apr. 2007), 8 pages.

Casanova, et al., "Effect of magnetic field on phosphorus centre in diamond," Physica Status Solidi A 186(2): 291-295 (Jul. 30, 2001), 6 pages.

Castelletto, et al., "Frontiers in diffraction unlimited optical methods for spin manipulation, magnetic field sensing and imaging using diamond nitrogen vacancy defects," Nanophotonics 1(2): 139-153 (Nov. 2012), 15 pages.

Chapman, et al., "Anomalous saturation effects due to optical spin depolarization in nitrogen-vacancy centers in diamond nanocrystals," Physical Review B 86(045204): 1-8 (Jul. 10, 2012), 8 pages.

Chavez, et al. "Detecting Arctic oil spills with NMR: a feasibility study." Near Surface Geophysics 13.4 (Feb. 2015): 409-416.

Chen et al., "Vector magnetic field sensing by a single nitrogen vacancy center in diamond," EPL 101(67003): 1-5 (Mar. 2013), 6 pages.

Chernobrod et al., "Improving the sensitivity of frequency modulation spectroscopy using nanomechanical cantilevers," Applied Physics Letters 85(17): 3896-3898 (Oct. 25, 2004), 3 pages.

Chernobrod et al., "Spin Microscope Based on Optically Detected Magnetic Resoncance," Journal of Applied Physics 97(014903): 1-3, (2005; first published online Dec. 10, 2004), 4 pages.

Childress et al., "Coherent dynamics of coupled electron and nuclear spin qubits in diamond," Science 314(5797): 281-285 (Oct. 13, 2006), 6 pages.

Chipaux et al., "Magnetic imaging with an ensemble of nitrogen vacancy-centers in diamond," European Physical Journal D 69(166): 1-10 (Jul. 2, 2015), 10 pages.

Chipaux et al., "Nitrogen vacancies (NV) centers in diamond for magnetic sensors and quantum sensing," SPIE 9370, Quantum Sensing and Nanophotonic Devices XII, 93701V (Feb. 8, 2015), 6 pages.

Chipaux, et al., "Wide bandwidth instantaneous radio frequency spectrum analyzer based on nitrogen vacancy centers in diamond," Applied Physics Letters 107(233502): 1-5 (2015), 6 pages.

Clevenson et al., "Broadband magnetometry and temperature sensing with a light-trapping diamond waveguide," Nature Physics 11: 393-397 (May 2015; first published online Apr. 6, 2015), 6 pages.

Constable, "Geomagnetic Spectrum, Temporal." In Encyclopedia of Geomagnetism and Paleomagnetism, pp. 353-355, Springer: Dordrecht, Netherlands (2007), 3 pages.

Cooper et al., "Time-resolved magnetic sensing with electronic spins in diamond," Nature Communications 5:3141: 1-7 (Jan. 24, 2014), 7 pages.

Creedon et al., "Strong coupling between P1 diamond impurity centers and a three-dimensional lumped photonic microwave cavity," Physical Review B 91(140408R): 1-5 (Apr. 24, 2015), 5 pages.

Dale, et al. "Medical applications of diamond magnetometry: commercial viability." arXiv preprint arXiv:1705.01994 (May 8, 2017), pp. 1-7.

Davies, "Current problems in diamond: towards a quantitative understanding," Physica B 273-274: 15-13 (Dec. 15, 1999), 9 pages.

De Lange et al., "Single-Spin Magnetometry with Multipulse Sensing Sequences," Physical Review Letters 106(080802): 1-4 (Feb. 24, 2011), 4 pages.

Degen, "Scanning magnetic field microscope with a diamond single-spin sensor," Applied Physics Letters 92(243111): 1-3 (Jun. 17, 2008), 3 pages.

Delacroix et al., "Design, manufacturing, and performance analysis of mid-infrared achromatic half-wave plates with diamond subwavelength gratings," Applied Optics 51(24): 5897-5902 (Aug. 16, 2012), 6 pages.

Denatale et al., "Fabrication and characterization of diamond moth eye antireflective surfaces on Ge," J. of Applied Physics 71: 1388-1393 (Mar. 1992), 8 pages.

(56) References Cited

OTHER PUBLICATIONS

Dobrovitski et al., "Quantum Control over Single Spins in Diamond," Annual Review of Condensed Matter Physics 4: 23-50 (Apr. 2013), 30 pages.
Doherty et al., "The nitrogen-vacancy colour centre in diamond," Physics Reports 528: 1-45 (Jul. 1, 2013), 45 pages.
Doherty et al., "Theory of the ground-state spin of the NV-center in diamond," Physical Review B 85(205203): 1-21 (May 3, 2012), 21 pages.
Doi et al., "Pure negatively charged state of the NV center in n-type diamond," Physical Review B 93(081203): 1-6 (Feb. 3, 2016), 6 pages.
Drake et al., "Influence of magnetic field alignment and defect concentration on nitrogen-vacancy polarization in diamond," New Journal of Physics 18(013011): 1-8 (Jan. 2016; first published on Dec. 24, 2015), 9 pages.
Dreau et al., "Avoiding power broadening in optically detected magnetic resonance of single NV defects for enhanced dc magnetic field sensitivity," Physical Review B 84(195204): 1-8 (Nov. 23, 2011), 8 pages.
Dreau et al., "High-resolution spectroscopy of single NV defects coupled with nearby 13C nuclear spins in diamond," Physical Review B 85(134107): 1-7 (Apr. 20, 2012), 7 pages.
Dumeige et al., "Magnetometry with nitrogen-vacancy ensembles in diamond based on infrared absorption in a doubly resonant optical cavity," Physical Review B 87(155202): 1-9 (Apr. 8, 2013), 9 pages.
Epstein et al., "Anisotropic interactions of a single spin and dark-spin spectroscopy in diamond," Nature Physics 1:94-98 (Nov. 2005), 5 pages.
Fallah et al., "Multi-sensor approach in vessel magnetic wake imaging," Wave Motion 51(1): 60-76 (Jan. 2014), retrieved from http://www.sciencedirect.com/science/article/pii/S0165212513001133 (Aug. 21, 2016).
Fedotov et al., "High-resolution magnetic field imaging with a nitrogen-vacancy diamond sensor integrated with a photonic-crystal fiber," Optics Letters 41(3): 472-475 (Feb. 1, 2016; published Jan. 25, 2016), 4 pages.
Fedotov et al., "Photonic-crystal-fiber-coupled photoluminescence interrogation of nitrogen vacancies in diamond nanoparticles," Laser Physics Letters 9(2): 151-154 (Feb. 2012; first published online Dec. 2, 2011), 5 pages.
Feng & Wei, "A steady-state spectral method to fit microwave absorptions of NV centers in diamonds: application to sensitive magnetic field sensing," Measurement Science & Technology 25(105102): 1-6 (Oct. 2014; first published online Aug. 29, 2014), 7 pages.
Fologea, et al. "Detecting single stranded DNA with a solid state nanopore." Nano Letters 5.10 (Aug. 15, 2005): 1905-1909.
Freitas, et al., "Solid-State Nuclear Magnetic Resonance (NMR) Methods Applied to the Study of Carbon Materials," Chemistry and Physics of Carbon, vol. 31 (2012), 45 pages.
Gaebel, et al. "Room-temperature coherent coupling of single spins in diamond." Nature Physics 2.6 (May 28, 2006): 408-413.
GB Examination Report from United Kingdom application No. GB 1618202.4 dated Jan. 10, 2017.
Geiselmann et al., "Fast optical modulation of the fluorescence from a single nitrogen-vacancy centre," Nature Physics 9: 785-789 (Dec. 2013; first published online Oct. 13, 2013), 5 pages.
Gombert & Blasi, "The Moth-Eye Effect-From Fundamentals to Commercial Exploitation," Functional Properties of Bio-Inspired Surfaces: 79-102, (Nov. 2009), 26 pages.
Gong et al., "Generation of Nitrogen-Vacancy Center Pairs in Bulk Diamond by Molecular Nitrogen Implantation," Chinese Physics Letters 33(2)(026105): 1-4 (Feb. 2016), 5 pages.
Gould et al., "An imaging magnetometer for bio-sensing based on nitrogen-vacancy centers in diamond," SPIE 8933, Frontiers in Biological Detection: From Nanosensors to Systems VI, 89330L (Mar. 18, 2014), 8 pages.
Gould et al., "Room-temperature detection of a single 19 nm superparamagnetic nanoparticle with an imaging magnetometer," Applied Physics Letters 105(072406): 1-4 (Aug. 19, 2014), 5 pages.
Gruber et al., "Scanning confocal optical microscopy and magnetic resonance on single defect centers," Science 276(5321): 2012-2014 (Jun. 27, 1997), 4 pages.
Haeberle et al., "Nanoscale nuclear magnetic imaging with chemical contrast," Nature Nanotechnology 10: 125-128 (Feb. 2015; first published online Jan. 5, 2015), 4 pages.
Haihua et al., "Design of wideband anti-reflective sub wavelength nanostructures," Infrared and Laser Engineering 40(2): 267-270 (Feb. 2011), 4 pages.
Hall et al., "Sensing of Fluctuating Nanoscale Magnetic Fields Using Nitrogen-Vacancy Centers in Diamond," Physical Review Letters 103(220802): 1-4 (Nov. 25, 2009), 4 pages.
Hanson et al., "Coherent Dynamics of a Single Spin Interacting with an Adjustable Spin Bath," Science 320(5874): 352-355 (Apr. 18, 2008), 5 pages.
Hanson et al., "Polarization and Readout of Coupled Single Spins in Diamond," Physical Review Letters 97(087601): 1-4 (Aug. 23, 2006), 4 pages.
Hanson et al., "Room-temperature manipulation and decoherence of a single spin in diamond," Physical Review 74(161203): 1-4 (Oct. 26, 2006), 4 pages.
Hanzawa et al., "Zeeman effect on the zero-phonon line of the NV center in synthetic diamond," Physica B 184(1-4): 137-140 (Feb. 1993), 4 pages.
Heerema, et al. "Graphene nanodevices for DNA sequencing." Nature nanotechnology 11.2 (Feb. 3, 2016): 127-136.
Hegyi & Yablonovitch, "Molecular imaging by optically detected electron spin resonance of nitrogen-vacancies in nanodiamonds," Nano Letters 13(3): 1173-1178 (Mar. 2013; first published online Feb. 6, 2013), 6 pages.
Hegyi & Yablonovitch, "Nanodiamond molecular imaging with enhanced contrast and expanded field of view," Journal of Biomedical Optics 19(1)(011015): 1-8 (Jan. 2014), 9 pages.
Hilser et al., "All-optical control of the spin state in the NV- center in diamond," Physical Review B 86(125204): 1-8 (Sep. 14, 2012), 8 pages.
Hobbs, "Study of the Environmental and Optical Durability of AR Microstructures in Sapphire, ALON, and Diamond," SPIE 7302, Window and Dome Technologies and Materials XI, 73020J (Apr. 27, 2009), 14 pages.
Huebener et al., "ODMR of NV centers in nano-diamonds covered with N@C60," Physica Status Solidi B 245(10): 2013-2017 (Oct. 2008; first published online Sep. 8, 2008), 5 pages.
Huxter et al., "Vibrational and electronic dynamics of nitrogen-vacancy centres in diamond revealed by two-dimensional ultrafast spectroscopy," Nature Physics 9: 744-749 (Sep. 29, 2013), 6 pages.
International Search Report and Written Opinion from related PCT application PCT/US2017/035315 dated Aug. 24, 2017, 7 pages.
International Search Report and Written Opinion of the International Searching Authority dated Apr. 1, 2016 from related PCT application PCT/US2016/014384, 12 pages.
International Search Report and Written Opinion of the International Searching Authority dated Apr. 11, 2016 from related PCT application PCT/US2016/014376, 12 pages.
International Search Report and Written Opinion of the International Searching Authority dated Apr. 11, 2016 from related PCT application PCT/US2016/014388, 14 pages.
International Search Report and Written Opinion of the International Searching Authority dated Apr. 11, 2016 from related PCT application PCT/US2016/014395, 15 pages.
International Search Report and Written Opinion of the International Searching Authority dated Apr. 4, 2017 from related PCT application PCT/US16/68366, 9 pages.
International Search Report and Written Opinion of the International Searching Authority dated Feb. 15, 2017 from related PCT application PCT/US2016/014390, 20 pages.
International Search Report and Written opinion of the International Searching Authority dated Jul. 12, 2016, from related PCT application PCT/US2016/014287, 14 pages.

(56) References Cited

OTHER PUBLICATIONS

International Search Report and Written Opinion of the International Searching Authority dated Jul. 16, 2015, from related PCT application PCT/US2015/24723, 8 pages.
International Search Report and Written Opinion of the International Searching Authority dated Jul. 6, 2015, from related PCT application PCT/US2015/021093, 9 pages.
International Search Report and Written Opinion of the International Searching Authority dated Jul. 8, 2015, from related PCT application PCT/US2015/024265, 11 pages.
International Search Report and Written Opinion of the International Searching Authority dated Jun. 1, 2017, from related PCT application PCT/US17/21811, 9 pages.
International Search Report and Written Opinion of the International Searching Authority dated Jun. 1, 2017, in related PCT application PCT/US17/22279, 20 pages.
International Search Report and Written Opinion of the International Searching Authority dated Jun. 10, 2016 from related PCT application PCT/US2016/014290, 11 pages.
International Search Report and Written Opinion of the International Searching Authority dated Jun. 15, 2017, from related PCT application PCT/US2017/024175, 10 pages.
International Search Report and Written Opinion of the International Searching Authority dated Jun. 2, 2016, from related PCT application PCT/US2016/014386, 14 pages.
International Search Report and Written Opinion of the International Searching Authority dated Jun. 2, 2016, from related PCT application PCT/US2016/014387, 13 pages.
International Search Report and Written Opinion of the International Searching Authority dated Jun. 6, 2016, from related PCT application PCT/US2016/014291, 13 pages.
International Search Report and Written Opinion of the International Searching Authority dated Jun. 9, 2016 from related PCT application PCT/US2016/014333, 16 pages.
International Search Report and Written Opinion of the International Searching Authority dated Jun. 9, 2017, from related patent application PCT/US2017/024181, 13 pages.
International Search Report and Written Opinion of the International Searching Authority dated Jun. 9, 2017, from related PCT application PCT/US2017/024179, 9 pages.
International Search Report and Written Opinion of the International Searching Authority dated Mar. 13, 2017 from related PCT application PCT/US2016/68320, 10 pages.
International Search Report and Written Opinion of the International Searching Authority dated Mar. 24, 2016 from related PCT application PCT/US2016/014336, 17 pages.
International Search Report and Written Opinion of the International Searching Authority dated Mar. 24, 2016 from related PCT application PCT/US2016/014297, 15 pages.
International Search Report and Written Opinion of the International Searching Authority dated Mar. 24, 2016 from related PCT application PCT/US2016/014392, 8 pages.
International Search Report and Written Opinion of the International Searching Authority dated Mar. 24, 2016 from related PCT application PCT/US2016/014403, 10 pages.
International Search Report and Written Opinion of the International Searching Authority dated Mar. 25, 2016, from related PCT application PCT/US2016/014363, 8 pages.
International Search Report and Written Opinion of the International Searching Authority dated Mar. 25, 2016, from related PCT application PCT/US2016/014389, 19 pages.
International Search Report and Written Opinion of the International Searching Authority dated Mar. 27, 2017 from related PCT application PCT/US16/68344, 16 pages.
International Search Report and Written Opinion of the International Searching Authority dated Mar. 28, 2016, from related PCT application PCT/US2016/014380, 9 pages.
International Search Report and Written Opinion of the International Searching Authority dated Mar. 28, 2016, from related PCT application PCT/US2016/014394, 17 pages.
International Search Report and Written Opinion of the International Searching Authority dated Mar. 29, 2016 from related PCT application PCT/US2016/014325, 11 pages.
International Search Report and Written Opinion of the International Searching Authority dated Mar. 29, 2016 from related PCT application PCT/US2016/014330, 8 pages.
International Search Report and Written Opinion of the International Searching Authority dated Mar. 29, 2016, from related PCT application PCT/US2016/014328, 7 pages.
International Search Report and Written Opinion of the International Searching Authority dated Mar. 29, 2016, from related PCT application PCT/US2016/014385, 11 pages.
International Search Report and Written Opinion of the International Searching Authority dated Mar. 30, 2016 from related PCT application PCT/US2016/014298, 14 pages.
International Search Report and Written Opinion of the International Searching Authority dated Mar. 31, 2016 from related PCT application PCT/US2016/014375, 11 pages.
International Search Report and Written Opinion of the International Searching Authority dated Mar. 31, 2016 from related PCT application PCT/US2016/014396, 11 pages.
International Search Report and Written Opinion of the International Searching Authority dated Mar. 31, 2017 from related PCT application PCT/US2016/066566, 11 pages.
International Search Report and Written Opinion of the International Searching Authority dated May 10, 2017 from related PCT application PCT/US17/19411, 8 pages.
International Search Report and Written Opinion of the International Searching Authority dated May 18, 2017, from related PCT application PCT/US2017/021593, 10 pages.
International Search Report and Written Opinion of the International Searching Authority dated May 19, 2017, from related PCT application PCT/US17/18099, 16 pages.
International Search Report and Written Opinion of the International Searching Authority dated May 26, 2016, from related PCT application PCT/US2016/014331, 15 pages.
International Search Report and Written Opinion of the International Searching Authority dated May 3, 2017 from related PCT application PCT/US2017/018701, 8 pages.
International Search Report and Written Opinion of the International Searching Authority dated May 4, 2017 from related PCT application PCT/US2017/018709, 8 pages.
International Search Report and Written Opinion of the International Searching Authority dated May 8, 2017 from related PCT application PCT/US2017/17321, 17 pages.
International Search Report and Written Opinion of the International Searching Authority dated Sep. 13, 2016, from related PCT application PCT/US16/14377, 11 pages.
International Search Report and Written Opinion of the International Searching Authority dated Jul. 14, 2017, from related PCT application PCT/US2017/022118, 13 pages.
International Search Report and Written Opinion of the International Searching Authority dated Jul. 17, 2017, from related PCT application PCT/US2017/024177, 11 pages.
International Search Report and Written Opinion of the International Searching Authority dated Jul. 18, 2017, from related PCT application PCT/US2017/024167, 11 pages.
International Search Report and Written Opinion of the International Searching Authority dated Jul. 18, 2017, from related PCT application PCT/US2017/024173, 13 pages.
International Search Report and Written Opinion of the International Searching Authority dated Jul. 19, 2017, from related PCT application PCT/US2017/024171, 12 pages.
International Search Report and Written Opinion of the International Searching Authority dated Jun. 15, 2017, from related PCT application PCT/US2017/024182, 21 pages.
International Search Report and Written Opinion of the International Searching Authority dated Jun. 22, 2017, in related PCT application PCT/US2017/024180, 10 pages.
International Search Report and Written Opinion of the International Searching Authority dated Jun. 5, 2017, from related PCT application PCT/US2017/024169, 11 pages.

(56) References Cited

OTHER PUBLICATIONS

International Search Report and Written Opinion of the International Searching Authority dated Jun. 5, 2017, from related PCT application PCT/US2017/024174, 8 pages.

International Search Report and Written Opinion of the International Searching Authority dated Jun. 5, 2017, in related PCT application PCT/US2017/024168, 7 pages.

International Search Report and Written Opinion of the International Searching Authority dated Jun. 6, 2017, from related PCT application PCT/2017/024165, 9 pages.

International Search Report and Written Opinion of the International Searching Authority dated Jun. 6, 2017, from related PCT application PCT/US2017/024172, 9 pages.

Ivady et al., "Pressure and temperature dependence of the zero-field splitting in the ground state of NV centers in diamond: A first-principles study," Physical Review B 90(235205): 1-8 (Dec. 2014), 8 pages.

Jarmola et al., "Temperature- and Magnetic-Field-Dependent Longitudinal Spin Relaxation in Nitrogen-Vacancy Ensembles in Diamond," Physical Review Letters 108 (197601): 1-5 (May 2012), 5 pages.

Jensen et al., "Light narrowing of magnetic resonances in ensembles of nitrogen-vacancy centers in diamond," Physical Review B 87(014115): 1-10 (Jan. 2013), 10 pages.

Kailath, "Linear Systems," Prentice Hall, (1979), 6 pages.

Karlsson et al., "Diamond micro-optics: microlenses and antireflection structures surfaces for the infrared spectral region," Optics Express 11(5): 502-507 (Mar. 10, 2003), 6 pages.

Keyser "Enhancing nanopore sensing with DNA nanotechnology." Nature nanotechnology 11.2 (Feb. 2016): 106-108.

Khan & Hemmer, "Noise limitation in nano-scale imaging," Proceedings of SPIE vol. 5842: 302-305, (Dec. 2005), 7 pages.

Kim et al., "Electron spin resonance shift and linewidth broadening of nitrogen-vacancy centers in diamond as a function of electron irradiation dose," Applied Physics Letters 101(082410): 1-5 (Aug. 2012), 6 pages.

Kim et al., "Jahn-Teller Splitting and Zeeman Effect of Acceptors in Diamond," Physica B 273-274: 647-627 (Jul. 1999), 4 pages.

Kim et al., "Magnetospectroscopy of acceptors in 'blue' diamonds," Physica B 302-301: 88-100 (Aug. 2001), 13 pages.

Kim et al., "Zeeman effect of electronic Raman lines of accepters in elemental semiconductors: Boron in blue diamond," Physical Review B 62(12): 8038-8052 (Sep. 2000), 15 pages.

King et al., "Optical polarization of 13C nuclei in diamond through nitrogen vacancy centers," Physical Review B 81(073201): 1-4 (Feb. 2010), 4 pages.

Kok et al., "Materials Science: Qubits in the pink," Nature 444(2): 49 (Nov. 2006), 1 page.

Konenko et al., "Formation of antireflective surface structures on diamond films by laser patterning," Applied Physics A 68:99-102 (Jan. 1999), 4 pages.

Kraus et al., "Magnetic field and temperature sensing with atomic-scale spin defects in silicon carbide," Scientific Reports 4(5303): 1-8 (Jul. 2014), 8 pages.

Lai et al., "Influence of a static magnetic field on the photoluminescence of an ensemble of nitrogen-vacancy color centers in a diamond single-crystal," Applied Physics Letters 95, (Sep. 2009), 4 pages.

Lai et al., "Optically detected magnetic resonance of a single Nitrogen-Vacancy electronic spin in diamond nanocrystals," CLEO/EQEC, (Jun. 14-19, 2009), 1 page.

Laraoui et al., "Nitrogen-vacancy assisted magnetometry of paramagnetic centers in an individual diamond nanocrystal," Nano Letters 12: 3477-3482 (Jul. 2012), 6 pages.

Lazariev et al., "A nitrogen-vacancy spin based molecular structure microscope using multiplexed projection reconstruction," Scientific Reports 5(14130): 1-8 (Sep. 2015), 8 pages.

Le Sage et al., "Efficient photon detection from color centers in a diamond optical waveguide," Phys. Rev. B 85: 121202(R), pp. 121202-1-121202-4, (Mar. 23, 2012), 4 pages.

Lee et al., "Vector magnetometry based on S=3/2 electronic spins," Physical Review B 92 (115201): 1-7 (Sep. 2015), 7 pages.

Lesik et al., "Preferential orientation of NV defects in CVD diamond films grown on (113)-oriented substrates," Diamond and Related Materials 56: 47-53 (Jun. 2015), 7 pages.

Levchenko et al., "Inhomogeneous broadening of optically detected magnetic resonance of the ensembles of nitrogen-vacancy centers in diamond by interstitial carbon atoms," Applied Physics Letters 106, (Mar. 2015; published online Mar. 9, 2015), 6 pages.

Lindsay "The promises and challenges of solid-state sequencing." Nature nanotechnology 11.2 (Feb. 2016): 109-111.

Liu et al., "Electron spin studies of nitrogen vacancy centers in nanodiamonds," Acta Physica Sinica 62(16) 164208: 1-5 (Aug. 2013), 5 pages.

Liu et al., "Fiber-integrated diamond-based magnetometer," Applied Physics Letters 103(143105): 1-4 (Sep. 2013), 5 pages.

MacLaurin et al., "Nanoscale magnetometry through quantum control of nitrogen-vacancy centres in rotationally diffusing nanodiamonds," New Journal of Physics 15, (Jan. 2013), 16 pages.

MacQuarie et al., "Mechanical spin control of nitrogen-vacancy centers in diamond," Retrieved from http://www.arxiv.org/pdf/1306.6356.pdf, pp. 1-8, (Jun. 2013), 8 pages.

Macs et al., "Diamond as a magnetic field calibration probe," Journal of Physics D: Applied Physics 37, (Apr. 2004; published Mar. 17, 2004), 6 pages.

Maletinsky et al., "A robust scanning diamond sensor for nanoscale imaging with single nitrogen-vacancy centres," Nature Nanotechnology 7: 320-324, (May 2012; published Apr. 15, 2012), 5 pages.

Mamin et al., "Multipulse Double-Quantum Magnetometry with Near-Surface Nitrogen-Vacancy Centers," Physical Review Letters 13(030803): 1-5 (Jul. 2014), 5 pages.

Mamin et al., "Nanoscale Nuclear Magnetic Resonance with a Nitrogen-Vacancy Spin Sensor," Science 339, (Feb. 2013), 5 pages.

Manson et al., "GR transitions in diamond: magnetic field measurements," Journal of Physics C Solid St. Phys 13: L1005-L1009, (Nov. 1980), 6 pages.

Massachusetts Institute of Technology, "Wide-Field Imaging Using Nitrogen Vacancies," in Patent Application Approval Process, Physics Week: 1-5, (Jan. 20, 2015), 5 pages.

Matlashov, et al. "SQUIDs for magnetic resonance imaging at ultra-low magnetic field." PIERS online 5.5 (2009): 466-470.

Matlashov, et al. "SQUIDs vs. induction coils for ultra-low field nuclear magnetic resonance: experimental and simulation comparison." IEEE Transactions on Applied Superconductivity 21.3 (Jan. 1, 2012): 465-468.

Matsuda et al., "Development of a plastic diamond anvil cell for high pressure magneto-photoluminescence in pulsed high magnetic fields," International Journal of Modern Physics B 18(27-29), (Nov. 2004), 7 pages.

Maze et al., "Nanoscale magnetic sensing using spin qubits in diamond," Proc. SPIE 7225, Advanced Optical Concepts in Quantum Computing, Memory, and Communication II, 722509 (Feb. 2, 2009) 8 pages.

Maze et al., "Nanoscale magnetic sensing with an individual electronic spin in diamond," Nature Physics 455: 644-647 (Oct. 2, 2008), 5 pages.

Meijer et al., "Generation of single color centers by focused nitrogen implantation," Applied Physics Letters 87(261909): 1-3 (Dec. 2005), 4 pages.

Michaelovich et al., "Polarization Dependencies of the Nitrogen-Vacancy Center." Undergraduate Project Report, Ben-Gurion University, Aug. 2015, pp. 1-9.

Millot et al., "High-field Zeeman and Paschen-Back effects at high pressure in oriented ruby," Physical Review B 78 (155125): 1-7 (Oct. 2008), 7 pages.

Moessle, et al. "SQUID-detected magnetic resonance imaging in microtesla fields." Annu. Rev. Biomed. Eng. 9 (May 23, 2008): 389-413.

Moriyama et al., "Importance of electron-electron interactions and Zeeman splitting in single-wall carbon nanotube quantum dots," Physica E 26: 473-476 (Feb. 2005), 4 pages.

(56) References Cited

OTHER PUBLICATIONS

Mrozek et al., "Circularly polarized microwaves for magnetic resonance study in the GHz range: Application to nitrogen-vacancy in diamonds," Applied Physics Letters, pp. 1-4 (Jul. 2015), 4 pages.

Nagl et al., "Improving surface and defect center chemistry of fluorescent nanodiamonds for imaging purposes-a review," Analytical and Bioanalaytical Chemistry 407: 7521-7536 (Oct. 2015; published online Jul. 29, 2015), 16 pages.

Neumann et al., "Excited-state spectroscopy of single NV defects in diamond using optically detected magnetic resonance," New Journal of Physics 11(013017): 1-10, (Jan. 2009), 11 pages.

Nizovtsev & Kilin, "Optically Detected Magnetic Resonance Spectra of the 14NV-13C Spin Systems in Diamond: Analytical Theory and Experiment," Doklady of the National Academy of Sciences of Belarus, (2013), 27 pages with English machine translation.

Nizovtsev et al., "Modeling fluorescence of single nitrogen-vacancy defect centers in diamond," Physica B—Condensed Matter, 608-611 (Dec. 2001), 4 pages.

Nizovtsev et al., "Theoretical study of hyperfine interactions and optically detected magnetic resonance spectra by simulation of the C-291(NV)H-(172) diamond cluster hosting nitrogen-vacancy center," New Journal of Physics 16(083014): 1-21 (Aug. 2014), 22 pages.

Nobauer et al., "Smooth optimal quantum control for robust solid state spin magnetometry," Retrieved from http://www.arxiv.org/abs/1412.5051, pp. 1-12, (Dec. 2014), 12 pages.

Nowodzinski et al., "Nitrogen-Vacancy centers in diamond for current imaging at the redistributive layer level of Integrated Circuits," Microelectronics Reliability 55: 1549-1553 (Aug. 2015), 5 pages.

Nusran et al., "Optimizing phase-estimation algorithms for diamond spin magnetometry," Physical Review B 90(024422): 1-12 (Jul. 2014), 12 pages.

Ohashi et al., "Negatively Charged Nitrogen-Vacancy Centers in a 5 nm Thin 12C Diamond Film," Nano Letters 13: 4733-4738 (Oct. 2013), 6 pages.

Pelliccione, et al., Two-dimensional nanoscale imaging of gadolinium spins via scanning probe relaxometry with a single spin in diamond, Phys. Rev. Applied 2.5, (Sep. 8, 2014): 054014 pp. 1-17.

Plakhotnik et al., "Super-Paramagnetic Particles Chemically Bound to Luminescent Diamond : Single Nanocrystals Probed with Optically Detected Magnetic Resonance," Journal of Physical Chemistry C 119: 20119-20124 (Aug. 2015), 6 pages.

Polatomic. "AN/ASQ-233A Digital Magnetic Anomaly Detective Set." Retrieved May 9, 2016, from http://polatomic.com/images/DMAD_Data_Sheet_09-2009.pdf (2009), 1 page.

Poole, "What is GMSK Modulation—Gaussian Minimum Shift Keying." Radio-Electronics, retrieved from https://web.archive.org/web/20150403045840/http://www.radio-electronics.com/info/rf-technology-design/pm-phase-modulation/what-is-gmsk-gaussian-minimum-shift-keyingtutorial.php (Apr. 3, 2015), 4 pages.

Qiu et al., "Low-field NMR Measurement Procedure when SQUID Detection is Used," IEEE/CSC & ESAS European Superconductivity News Forum, No. 5, Jul. 2008.

Qiu, et al. "SQUID-detected NMR in Earth's magnetic field." Journal of Physics: Conference Series. vol. 97. No. 1. IOP Publishing, Mar. 2008, pp. 1-7.

Rabeau et al., "Implantation of labelled single nitrogen vacancy centers in diamond using 15N," Applied Physics Letters 88, (Jan. 2006), 4 pages.

Ramsey, et al., "Phase Shifts in the Molecular Beam Method of Separated Oscillating Fields", Physical Review, vol. 84, No. 3, Nov. 1, 1951, pp. 506-507.

Ranjbar et al., "Many-electron states of nitrogen-vacancy centers in diamond and spin density calculations," Physical Review B 84(165212): 1-6 (Oct. 2011), 6 pages.

Reynhardt, "Spin-lattice relaxation of spin-1/2 nuclei in solids containing diluted paramagnetic impurity centers. I. Zeeman polarization of nuclear spin system," Concepts in Magnetic Resonance Part A, pp. 20-35, (Sep. 2003), 16 pages.

Rogers et al., "Singlet levels of the NV(-) centre in diamond," New Journal of Physics 17, (Jan. 2015), 13 pages.

Rondin et al., "Magnetometry with nitrogen-vacancy defects in diamond," Reports on Progress in Physics 77(056503) 1-26 (May 2014), 27 pages.

Rondin et al., "Magnetometry with nitrogen-vacancy defects in diamond." May 22, 2014 (May 22, 2014), pp. 1 [online] http://arxiv.org/pdf/1311.5214.pdf, 29 pages.

Rondin et al., "Nanoscale magnetic field mapping with a single spin scanning probe magnetometer," Applied Physics Letters 100, (Apr. 2012), 5 pages.

Sarkar et al., "Magnetic properties of graphite oxide and reduced graphene oxide," Physica E 64: 78-82 (Nov. 2014), 5 pages.

Scheuer et al., "Accelerated 2D magnetic resonance spectroscopy of single spins using matrix completion," Scientific Reports 5(17728): 1-8 (Dec. 2015), 8 pages.

Schirhagl et al., "Nitrogen-vacancy centers in diamond: Nanoscale sensors for physics and biology," Annual Review of Physical Chemistry 65: 83-105 (Jan. 2014), 26 pages.

Schoenfeld & Harneit, "Real time magnetic field sensing and imaging using a single spin in diamond," Physical Review Letters 106(030802): 1-4 (Jan. 2011), 4 pages.

Sedov et al., "Si-doped nano- and microcrystalline diamond films with controlled bright photoluminescence of silicon-vacancy color centers," Diamond and Related Materials 56: 23-28 (Jun. 2015; available online Apr. 18, 2015), 6 pages.

Shames et al., "Magnetic resonance tracking of fluorescent nanodiamond fabrication," Journal of Physics D: Applied Physics 48(155302): 1-13 (Apr. 2015; published Mar. 20, 2015), 14 pages.

Shao et al., "Diamond Color Center Based FM Microwave Demodulator," in Conference on Lasers and Electro-Optics, OSA Technical Digest (online) (Optical Society of America), paper JTh2A.136, (Jun. 5-10, 2016), 2 pages.

Sheinker et al., "Localization in 3-D Using Beacons of Low Frequency Magnetic Field." IEEE Transactions on Instrumentation and Measurement 62(12): 3194-3201 (Dec. 2013), 8 pages.

Simanovskaia et al., "Sidebands in optically detected magnetic resonance signals of nitrogen vacancy centers in diamond," Physical Review B 87(224106): 1-11 (Jun. 2013), 11 pages.

Sotoma et al., "Effective production of fluorescent nanodiamonds containing negatively-charged nitrogen-vacancy centers by ion irradiation," Diamond and Related Materials 49: 33-38 (Oct. 2014), 6 pages.

Soykal et al., "Quantum metrology with a single spin-3/2 defect in silicon carbide," Mesoscale and Nanoscale Physics (May 24, 2016), retrieved from https://arxiv.org/abs/1605.07628 (Sep. 22, 2016), 9 pages.

Steiner et al., "Universal enhancement of the optical readout fidelity of single electron spins at nitrogen-vacancy centers in diamond," Physical Review B 81(035205): 1-6 (Jan. 2010), 6 pages.

Steinert et al., "High-sensitivity magnetic imaging using an array of spins in diamond," Rev. Sci. Inst. 81(043705): 1-5 (Apr. 23, 2010), 5 pages.

Steinert et al., "Magnetic spin imaging under ambient conditions with sub-cellular resolution." Nature Comms 4:1607 (Mar. 19, 2013).

Stepanov et al., "High-frequency and high-field optically detected magnetic resonance of nitrogen-vacancy centers in diamond," Applied Physics Letters 106, (Feb. 2015), 5 pages.

Sternschulte et al., "Uniaxial stress and Zeeman splitting of the 1.681 eV optical center in a homoepitaxial CVD diamond film," Diamond and Related Materials 4: 1189-1192 (Sep. 1995), 4 pages.

Storteboom et al., "Lifetime investigation of single nitrogen vacancy centres in nanodiamonds," Optics Express 23(9): 11327-11333 (May 4, 2015; published Apr. 22, 2015), 7 pages.

Sushkov, et al. "All-optical sensing of a single-molecule electron spin." Nano letters 14.11 (Nov. 7, 2013): 6443-6448.

Tahara et al., "Quantifying selective alignment of ensemble nitrogen-vacancy centers in (111) diamond," Applied Physics Letters 107:193110 (Nov. 2015; published online Nov. 13, 2015), 5 pages.

Taylor et al., "High-sensitivity diamond magnetometer with nanoscale resolution," Nature Physics 4: 810-816 (Oct. 2008), 7 pages.

(56) References Cited

OTHER PUBLICATIONS

Teale, "Magnetometry with Ensembles of Nitrogen Vacancy Centers in Bulk Diamond," Master's Thesis, Massachusetts Institute of Technology Department of Electrical Engineering and Computer Science (Sep. 2015), 57 pages.
Terblanche et al., "13C spin-lattice relaxation in natural diamond: Zeeman relaxation at 4.7 T and 300 K due to fixed paramagnetic nitrogen defects," Solid State Nuclear Magnetic Resonance 20: 1-22 (Aug. 2001), 22 pages.
Terblanche et al., "13C spin-lattice relaxation in natural diamond: Zeeman relaxation in fields of 500 to 5000 G at 300 K due to fixed paramagnetic nitrogen defects," Solid State Nuclear Magnetic Resonance 19: 107-129 (May 2001), 23 pages.
Tetienne et al., "Magnetic-field-dependent photodynamics of single NV defects in diamond: an application to qualitative all-optical magnetic imaging," New Journal of Physics 14(103033): 1-5 (Oct. 2012), 16 pages.
Tetienne, et al. "Spin relaxometry of single nitrogen-vacancy defects in diamond nanocrystals for magnetic noise sensing." Physical Review B 87.23 (Apr. 3, 2013): 235436-1-235436-5.
Tong et al., "A hybrid-system approach for W state and cluster state generation," Optics Communication 310: 166-172, (Jan. 2014; available online Aug. 12, 2013), 7 pages.
Uhlen et al., "New diamond nanofabrication process for hard x-ray zone plates," J. of Vacuum Science & Tech. B 29(6) (06FG03): 1-4 (Nov./Dec. 2011), 4 pages.
U.S. Notice of Allowance dated Apr. 20, 2016, from related U.S. Appl. No. 15/003,718, 9 pages.
U.S. Notice of Allowance dated Aug. 11, 2017 from related U.S. Appl. No. 15/003,558, 5 pages.
U.S. Notice of Allowance dated Aug. 17, 2016, from related U.S. Appl. No. 15/003,718, 8 pages.
U.S. Notice of Allowance dated Dec. 13, 2016, from related U.S. Appl. No. 14/680,877, 8 pages.
U.S. Notice of Allowance dated Dec. 22, 2016, from related U.S. Appl. No. 14/659,498, 10 pages.
U.S. Notice of Allowance dated Feb. 14, 2017, from related U.S. Appl. No. 15/003,677, 8 pages.
U.S. Notice of Allowance dated Jul. 18, 2017 from related U.S. Appl. No. 15/003,634, 6 pages.
U.S. Notice of Allowance dated Jul. 24, 2017 from related U.S. Appl. No. 15/003,088, 12 pages.
U.S. Notice of Allowance dated Jun. 20, 2017, from related U.S. Appl. No. 15/204,675, 9 pages.
U.S. Notice of Allowance dated Jun. 28, 2017, from related U.S. Appl. No. 15/003,256, 10 pages.
U.S. Notice of Allowance dated Jun. 8, 2017, from related U.S. Appl. No. 15/351,862, 7 pages.
U.S. Notice of Allowance dated Mar. 15, 2017, from related U.S. Appl. No. 15/351,862, 6 pages.
U.S. Notice of Allowance dated Mar. 29, 2016, from related U.S. Appl. No. 15/003,590, 11 pages.
U.S. Notice of Allowance dated May 26, 2017 from related U.S. Appl. No. 15/218,821, 7 pages.
U.S. Notice of Allowance dated Sep. 1, 2017, from related U.S. Appl. No. 14/676,740, 7 pages.
U.S. Notice of Allowance dated Sep. 14, 2017, from related U.S. Appl. No. 15/476,636, 10 pages.
U.S. Notice of Allowance dated Sep. 18, 2017, from related U.S. Appl. No. 15/003,206, 11 pages.
U.S. Notice of Allowance dated Sep. 26, 2017, from related U.S. Appl. No. 15/003,281, 7 pages.
U.S. Notice of Allowance dated Sep. 8, 2016, from related U.S. Appl. No. 15/003,298, 10 pages.
U.S. Office Action dated Apr. 17, 2017, from related U.S. Appl. No. 15/003,558, 12 pages.
U.S. Office Action dated Aug. 15, 2017 from related U.S. Appl. No. 15/003,281, 12 pages.
U.S. Office Action dated Aug. 24, 2016 from related U.S. Appl. No. 14/676,740, 19 pages.
U.S. Office Action dated Feb. 10, 2017, from related U.S. Appl. No. 14/676,740, 20 pages.
U.S. Office Action dated Feb. 10, 2017, from related U.S. Appl. No. 15/003,088, 11 pages.
U.S. Office Action dated Feb. 16, 2017, from related U.S. Appl. No. 15/204,675, 7 pages.
U.S. Office Action dated Jul. 27, 2017 from related U.S. Appl. No. 15/003,577, 15 pages.
U.S. Office Action dated Jul. 29, 2016 from related U.S. Appl. No. 14/680,877, 8 pages.
U.S. Office Action dated Jun. 1, 2017, from related U.S. Appl. No. 15/003,797, 29 pages.
U.S. Office Action dated Jun. 1, 2017, from related U.S. Appl. No. 15/179,957, 29 pages.
U.S. Office Action dated Jun. 12, 2017, from related U.S. Appl. No. 15/003,256, 9 pages.
U.S. Office Action dated Jun. 12, 2017, from related U.S. Appl. No. 15/003,336, 14 pages.
U.S. Office Action dated Jun. 16, 2017, from related U.S. Appl. No. 15/003,678, 15 pages.
U.S. Office Action dated Jun. 2, 2017, from related U.S. Appl. No. 15/476,636, 10 pages.
U.S. Office Action dated Mar. 1, 2017, from related U.S. Appl. No. 15/003,634, 7 pages.
U.S. Office Action dated Mar. 16, 2017, from related U.S. Appl. No. 15/218,821, 7 pages.
U.S. Office Action dated May 13, 2016, from related U.S. Appl. No. 14/676,740, 15 pages.
U.S. Office Action dated May 22, 2017, from related U.S. Appl. No. 15/003,206, 12 pages.
U.S Office Action dated May 6, 2016, from related U.S. Appl. No. 14/659,498.
U.S. Office Action dated Nov. 2, 2016, from related U.S. Appl. No. 15/003,256, 19 pages.
U.S. Office Action dated Nov. 3, 2016, from related U.S. Appl. No. 15/204,675, 9 pages.
U.S. Office Action dated Oct. 14, 2016 from related U.S. Appl. No. 15/003,677, 13 pages.
U.S. Office Action dated Oct. 19, 2016, from related U.S. Appl. No. 15/218,821, 6 pages.
U.S. Office Action dated Sep. 27, 2017, from related U.S. Appl. No. 15/003,176, 8 pages.
U.S. Office Action dated Sep. 8, 2017, from related U.S. Appl. No. 15/003,292, 8 pages.
Vershovskii & Dmitriev, "Combined excitation of an optically detected magnetic resonance in nitrogen-vacancy centers in diamond for precision measurement of the components of a magnetic field vector," Technical Physics Letters 41(11): 1026-1029 (Nov. 2015), 4 pages.
Vershovskii & Dmitriev, "Micro-scale three-component quantum magnetometer based on nitrogen-vacancy color centers in diamond crystal," Technical Physics Letters 41(4): 393-396 (Apr. 2015), 4 pages.
Wahlstrom et al., "Modeling Magnetic Fields Using Gaussian Processes," 2013 IEEE International Conference on Acoustics, Speech, and Signal Processing, pp. 3522-3526 (May 26-31, 2013), 5 pages.
Wang et al., "Optimizing ultrasensitive single electron magnetometer based on nitrogen-vacancy center in diamond," Chinese Science Bulletin, 58(24): 2920-2923, (Aug. 2013), 4 pages.
Webber et al., "Ab initio thermodynamics calculation of the relative concentration of NV- and NV0 defects in diamond," Physical Review B 85,(014102): 1-7 (Jan. 2012), 7 pages.
Wells, et al. "Assessing graphene nanopores for sequencing DNA." Nano letters 12.8 (Jul. 10, 2012): 4117-4123.
Widmann et al., "Coherent control of single spins in silicon carbide at room temperature," Nature Materials, 14: 164-168 (2015) (available online Dec. 1, 2014), 5 pages.
Wolf et al., "Subpicotesla Diamond Magnetometry," Physical Review X 5(041001): 1-10 (Oct. 2015), 10 pages.
Wolfe et al., "Off-resonant manipulation of spins in diamond via precessing magnetization of a proximal ferromagnet," Physical Review B 89(180406): 1-5 (May 2014), 5 pages.

(56) References Cited

OTHER PUBLICATIONS

Wroble, "Performance Analysis of Magnetic Indoor Local Positioning System." Western Michigan University Master's Theses, Paper 609 (Jun. 2015), 42 pages.
Wysocki et al., "Modified Walsh-Hadamard sequences for DS CDMA wireless systems." Int. J. Adaptive Control and Signal Processing 16(8): 589-602 (Oct. 2002; first published online Sep. 23, 2002), 25 pages.
Xue & Liu, "Producing GHZ state of nitrogen-vacancy centers in cavity QED," Journal of Modern Optics 60(6-7), (Mar. 2013), 8 pages.
Yang & Gu, "Novel calibration techniques for high pulsed-magnetic fields using luminescence caused by photo," (with English machine translation), Journal of Huazhong University of Science and Technology, (Jun. 2007), 11 pages.
Yavkin et al., "Defects in Nanodiamonds: Application of High-Frequency cw and Pulse EPR, ODMR," Applied Magnetic Resonance, 45: 1035-1049 (Oct. 2014; published online Sep. 10, 2014), 15 pages.
Yu et al., "Bright fluorescent nanodiamonds: no photobleaching and low cytotoxicity," J. Am. Chem. Soc., 127: 17604-17605 (Nov. 25, 2005), 2 pages.
Zhang et al., "Laser-polarization-dependent and magnetically controlled optical bistability in diamond nitrogen-vacancy centers," Physics Letters A 377: 2621-2627 (Nov. 2013), 7 pages.
Zhang et al., "Laser-polarization-dependent spontaneous emission of the zero phonon line from single nitrogen-vacancy center in diamond," Chinese Physics B 24(3), (Apr. 2014), 13 pages.
Zhang et al., "Scalable quantum information transfer between nitrogen-vacancy-center ensembles," Annals of Physics, 355: 170-181 (Apr. 2015; available online Feb. 14, 2013), 12 pages.
Zhao et al., "Atomic-scale magnetometry of distant nuclear spin clusters via nitrogen-vacancy spin in diamond," Nature Nanotechnology, 5: 242-246 (Apr. 2011), 5 pages.
Bui et al., "Noninvasive Fault Monitoring of Electrical Machines by Solving the Steady-State Magnetic Inverse Problem," in IEEE Transactions on Magnetics, vol. 44, No. 6, pp. 1050-1053, Jun. 24, 2008.
Chadebec et al., "Rotor fault detection of electrical machines by low frequency magnetic stray field analysis," 2005 5th IEEE International Symposium on Diagnostics for Electric Machines, Power Electronics and Drives, Vienna, 2005, submitted Mar. 22, 2006, pp. 1-6.
Froidurot et al., "Magnetic discretion of naval propulsion machines," in IEEE Transactions on Magnetics, vol. 38, No. 2, pp. 1185-1188, Mar. 2002.
IEEE Std 802.11 TM-2012 Wireless LAN Medium Access Control (MAC) and Physical Layer (PHY) Specifications, 1 page.
Kwon et al., "Analysis of the far field of permanent-magnet motors and effects of geometric asymmetries and unbalance in magnet design," in IEEE Transactions on Magnetics, vol. 40, No. 2, pp. 435-442, Mar. 2004.
Maertz et al., "Vector magnetic field microscopy using nitrogen vacancy centers in diamond", Applied Physics Letters 96, No. 9, Mar. 1, 2010, pp. 092504-1-092504-3.
U.S. Notice of Allowance dated Feb. 2, 2018, from related U.S. Appl. No. 15/003,292, 8 pages.
U.S. Notice of Allowance dated Feb. 21, 2018, from related U.S. Appl. No. 15/003,176, 9 pages.
U.S. Office Action dated Feb. 1, 2018, from related U.S. Appl. No. 15/003,577, 16 pages.
U.S. Office Action dated Feb. 5, 2018, from related U.S. Appl. No. 15/450,504, 12 pages.
U.S. Office Action dated Jan. 25, 2018, from related U.S. Appl. No. 15/672,953, 28 pages.
U.S. Office Action dated Jan. 26, 2018, from related U.S. Appl. No. 15/003,678, 14 pages.
U.S. Office Action dated Mar. 27, 2018, from related U.S. Appl. No. 15/468,386, 21 pages.
U.S. Office Action dated Mar. 28, 2018, from related U.S. Appl. No. 15/003,177, 12 pages.
U.S. Office Action dated Mar. 5, 2018, from related U.S. Appl. No. 14/866,730, 14 pages.
U.S. Office Action dated Mar. 8, 2018, from related U.S. Appl. No. 15/380,691, 12 pages.
U.S. Office Action dated Mar. 8, 2018, from related U.S. Appl. No. 15/479,256, 30 pages.
Wegerich, "Similarity based modeling of time synchronous averaged vibration signals for machinery health monitoring," 2004 IEEE Aerospace Conference Proceedings (IEEE Cat. No. 04TH8720), 2004, pp. 3654-3662 vol. 6.
Wikipedia, "Continuous phase modulation", downloaded from https://web.archive.org/web/20151017015236/https://en.wikipedia.org/wiki/Continuous_phase_modulation on May 10, 2017, 3 pages.
Wikipedia, "Minimum-shift keying", downloaded from https://web.archive.org/web/20151017175828/https://en.wikipedia.org/wiki/Minimum-shift_keying on May 10, 2017, 2 pages.
European Extended Search Report for Appl. Ser. No. 16743879.5 dated Sep. 11, 2018, 11 pages.
European Extended Search Report for Appl. Ser. No. 16800410.9 dated Oct. 12, 2018, 11 pages.
Niu, "Crack Detection of Power Line Based on Metal Magnetic Memory Non-destructive", TELKOMNIKA Indonesian Journal of Electrical Engineering, vol. 12, No. 11, Nov. 1, 2014, pp. 7764-7771.
U.S. Final Office Action for U.S. Appl. No. 15/380,691 dated Sep. 21, 2018, 12 pages.
U.S. Final Office Action for U.S. Appl. No. 15/479,256 dated Sep. 10, 2018, 20 pages.
U.S. Non-Final Office Action for U.S. Appl. No. 15/443,422 dated Oct. 2, 2018, 16 pages.
U.S. Non-Final Office Action for U.S. Appl. No. 15/446,373 dated Oct. 1, 2018, 13 pages.
U.S. Non-Final Office Action for U.S. Appl. No. 15/454,162 dated Sep. 10, 2018, 13 pages.
U.S. Non-Final Office Action for U.S. Appl. No. 15/468,282 dated Oct. 10, 2018, 12 pages.
U.S. Non-Final Office Action for U.S. Appl. No. 15/372,201 dated Oct. 15, 2018, 12 pages.
U.S. Non-Final Office Action for U.S. Appl. No. 15/468,274 dated Oct. 26, 2018, 11 pages.
U.S. Notice of Allowance for U.S. Appl. No. 14/866,730 dated Aug. 15, 2018, 9 pages.
U.S. Notice of Allowance for U.S. Appl. No. 15/468,289 dated Oct. 17, 2018, 12 pages.
U.S. Notice of Allowance for U.S. Appl. No. 15/003,704 dated Nov. 2, 2018, 19 pages.
U.S. Office Action for U.S. Appl. No. 15/468,397 dated Sep. 13, 2018, 7 pages.
European Extended Search Report for Appl. Ser. No. 16740794.9 dated Nov. 12, 2018, 12 pages.
Halbach et al., "Design of Permanent Multipole Magnets with Oriented Rare Earth Cobalt Material", Nuclear Instruments and Methods, North Holland Publishing Co., Amsterdam, NL., vol. 169, Jan. 1, 1980, pp. 1-5, XP001032085, DOI: 10.1016/0029-554X(80)90094-4.
Hodges et al., "Time-keeping with electron spin states in diamond", Dept. of Electrical Engineering and Dept. of Applied Physics and Applied Mathematics, Columbia University, New York, New York 10027, Aug. 30, 2011, 13 pages.
Hodges et al., Appendix, "Time-keeping with electron spin states in diamond", Dept. of Electrical Engineering and Dept. of Applied Physics and Applied Mathematics, Columbia University, New York, New York 10027, Aug. 27, 2012, 46 pages.
International Search Report and Written Opinion for PCT Appl. Ser. No. PCT/US2018/041527 dated Feb. 4, 2019, 22 pages.
U.S. Ex Parte Quayle Action for U.S. Appl. No. 15/468,641 dated Nov. 28, 2018, 11 pages.
U.S. Non-Final Office Action for U.S. Appl. No. 15/003,177 dated Jan. 14, 2019, 15 pages.
U.S. Non-Final Office Action for U.S. Appl. No. 15/003,670 dated Nov. 27, 2018, 14 pages.

(56) References Cited

OTHER PUBLICATIONS

U.S. Non-Final Office Action for U.S. Appl. No. 15/382,045 dated Dec. 31, 2018, 16 pages.
U.S. Non-Final Office Action for U.S. Appl. No. 15/400,794 dated Jan. 10, 2019, 6 pages.
U.S. Non-Final Office Action for U.S. Appl. No. 15/468,356 dated Jan. 2, 2019, 10 pages.
U.S. Non-Final Office Action for U.S. Appl. No. 15/468,951 dated Dec. 13, 2018, 9 pages.
U.S. Notice of Allowance for U.S. Appl. No. 15/003,670 dated Feb. 1, 2019, 7 pages.
U.S. Notice of Allowance for U.S. Appl. No. 15/350,303 dated Dec. 26, 2018, 10 pages.
U.S. Notice of Allowance for U.S. Appl. No. 15/450,504 dated Dec. 13, 2018, 7 pages.
U.S. Notice of Allowance for U.S. Appl. No. 15/454,162 dated Jan. 17, 2019, 8 pages.
U.S. Notice of Allowance for U.S. Appl. No. 15/468,397 dated Dec. 12, 2018, 5 pages.
U.S. Notice of Allowance for U.S. Appl. No. 15/468,641 dated Feb. 7, 2019, 10 pages.
U.S. Notice of Allowance for U.S. Appl. No. 15/479,256 dated Feb. 4, 2019, 7 pages.
Teeling-Smith et al., "Electron Paramagnetic Resonance of a Single NV Nanodiamond Attached to an Individual Biomolecule", Biophysical Journal 110, May 10, 2016, pp. 2044-2052.
UK Office Action dated Jun. 8, 2018, from related application No. GB1617438.5, 3 pages.
U.S. Final Office Action dated Jul. 26, 2018 from related U.S. Appl. No. 15/003,177, 14 pages.
U.S. Non-Final Office Action dated Aug. 6, 2018 from related U.S. Appl. No. 15/376,244, 28 pages.
U.S. Non-Final Office Action dated Aug. 9, 2018 from related U.S. Appl. No. 15/003,309, 22 pages.
U.S. Non-Final Office Action dated Jul. 20, 2018 from related U.S. Appl. No. 15/350,303, 13 pages.
U.S. Non-Final Office Action dated Jul. 26, 2018 from related U.S. Appl. No. 15/380,419, 11 pages.
U.S. Non-Final Office Action dated Jul. 3, 2018 from related U.S. Appl. No. 15/003,396, 19 pages.
U.S. Notice of Allowance dated Jul. 18, 2018 from related U.S. Appl. No. 15/468,386, 12 pages.
U.S. Notice of Allowance dated Jul. 6, 2018 from related U.S. Appl. No. 15/672,953, 11 pages.
U.S. Notice of Allowance dated Jun. 27, 2018 from related U.S. Appl. No. 15/003,519, 21 pages.
U.S. Notice of Allowance dated May 15, 2018, from related U.S. Appl. No. 15/003,209, 7 pages.
U.S. Notice of Allowance dated May 16, 2018, from related U.S. Appl. No. 15/003,145, 8 pages.
U.S. Office Action dated Jun. 19, 2018, from related U.S. Appl. No. 15/450,504, 12 pages.
U.S. Appl. No. 14/659,498, filed Mar. 16, 2015, U.S. Pat. No. 9,638,821.
PCT/US2015/021093, Mar. 17, 2015, WO2015142945.
U.S. Appl. No. 14/676,740, filed Apr. 1, 2015, 20150326410.
PCT/US2015/024265, Apr. 3, 2015, WO2015157110.
PCT/US2015/024723, Apr. 7, 2015, WO2015157290.
U.S. Appl. No. 14/680,877, filed Apr. 7, 2015, U.S. Pat. No. 9,590,601.
U.S. Appl. No. 14/866,730, filed Sep. 25, 2015, 20160146904.
U.S. Appl. No. 15/003,678, filed Jan. 21, 2016, 20170212183.
U.S. Appl. No. 15/003,281, filed Jan. 21, 2016, 20170212178.
U.S. Appl. No. 15/003,292, filed Jan. 21, 2016, 20170212179.
U.S. Appl. No. 15/003,298, filed Jan. 21, 2016, U.S. Pat. No. 9,551,763.
U.S. Appl. No. 15/003,309, filed Jan. 21, 2016, 20170212180.
U.S. Appl. No. 15/003,176, filed Jan. 21, 2016, 20170123015.
U.S. Appl. No. 15/003,145, filed Jan. 21, 2016, 20170199156.
U.S. Appl. No. 15/003,336, filed Jan. 21, 2016, 20170212181.
U.S. Appl. No. 15/003,558, filed Jan. 21, 2016, 20170146617.
U.S. Appl. No. 15/003,519, filed Jan. 21, 2016, 20170146616.
U.S. Appl. No. 15/003,677, filed Jan. 21, 2016, U.S. Pat. No. 9,614,589.
U.S. Appl. No. 15/003,256, filed Jan. 21, 2016, 20170212177.
U.S. Appl. No. 15/003,577, filed Jan. 21, 2016, 20170212046.
U.S. Appl. No. 15/003,704, filed Jan. 21, 2016, 20160231394.
U.S. Appl. No. 15/003,718, filed Jan. 21, 2016, U.S. Pat. No. 9,541,610.
U.S. Appl. No. 15/003,062, filed Jan. 21, 2016, 20170023487.
U.S. Appl. No. 15/003,652, filed Jan. 21, 2016, 20170010594.
U.S. Appl. No. 15/003,634, filed Jan. 21, 2016, 20170212182.
U.S. Appl. No. 15/003,670, filed Jan. 21, 2016, 20170212190.
U.S. Appl. No. 15/003,088, filed Jan. 21, 2016, 20160214714.
U.S. Appl. No. 15/003,797, filed Jan. 21, 2016, 20160216341.
U.S. Appl. No. 15/003,590, filed Jan. 21, 2016, U.S. Pat. No. 9,557,391.
U.S. Appl. No. 15/003,206, filed Jan. 21, 2016, 20170110015.
U.S. Appl. No. 15/003,193, filed Jan. 21, 2016, 20160216304.
U.S. Appl. No. 15/003,617, filed Jan. 21, 2016, 20170010334.
U.S. Appl. No. 15/003,396, filed Jan. 21, 2016, 20170068012.
U.S. Appl. No. 15/003,177, filed Jan. 21, 2016, 20170212258.
U.S. Appl. No. 15/003,209, filed Jan. 21, 2016, 20170211947.
PCT/US2016/014389, Jan. 21, 2016, WO2017078766.
PCT/US2016/014336, Jan. 21, 2016, WO2016118756.
PCT/US2016/014403, Jan. 21, 2016, WO2016118791.
PCT/US2016/014331, Jan. 21, 2016, WO2016126435.
PCT/US2016/014387, Jan. 21, 2016, WO2017014807.
PCT/US2016/014390, Jan. 21, 2016, WO2016190909.
PCT/US2016/014385, Jan. 21, 2016, WO2016122966.
PCT/US2016/014375, Jan. 21, 2016, WO2016122965.
PCT/US2016/014298, Jan. 21, 2016, WO2017007514.
PCT/US2016/014297, Jan. 21, 2016, WO2017007513.
PCT/US2016/014377, Jan. 21, 2016, WO2017039747.
PCT/US2016/014392, Jan. 21, 2016, WO2017127095.
PCT/US2016/014395, Jan. 21, 2016, WO2017127097.
PCT/US2016/014394, Jan. 21, 2016, WO2017127096.
PCT/US2016/014386, Jan. 21, 2016, WO2017127094.
PCT/US2016/014333, Jan. 21, 2016, WO2016126436.
PCT/US2016/014328, Jan. 21, 2016, WO2017087014.
PCT/US2016/014325, Jan. 21, 2016, WO2017087013.
PCT/US2016/014330, Jan. 21, 2016, WO2017127085.
PCT/US2016/014388, Jan. 21, 2016, WO2017095454.
PCT/US2016/014380, Jan. 21, 2016, WO2017123261.
PCT/US2016/014290, Jan. 21, 2016, WO2017127080.
PCT/US2016/014363, Jan. 21, 2016, WO2017127090.
PCT/US2016/014287, Jan. 21, 2016, WO2017127079.
PCT/US2016/014291, Jan. 21, 2016, WO2017127081.
PCT/US2016/014396, Jan. 21, 2016, WO2017127098.
PCT/US2016/014384, Jan. 21, 2016, WO2017127093.
PCT/US2016/014376, Jan. 21, 2016, WO2017127091.
U.S. Appl. No. 15/179,957, filed Jun. 10, 2016, 20160356863.
U.S. Appl. No. 15/207,457, filed Jul. 11, 2016.
U.S. Appl. No. 15/218,821, filed Jul. 25, 2016, 20170212185.
U.S. Appl. No. 15/204,675, filed Jul. 7, 2016, 20170212184.
U.S. Appl. No. 15/350,303, filed Nov. 14, 2016.
U.S. Appl. No. 15/351,862, filed Nov. 15, 2016, U.S. Pat. No. 9,720,055.
U.S. Appl. No. 15/372,201, filed Dec. 7, 2016, 20170212187.
U.S. Appl. No. 15/376,244, filed Dec. 12, 2016.
U.S. Appl. No. 15/380,691, filed Dec. 15, 2016.
U.S. Appl. No. 15/382,045, filed Dec. 16, 2016.
U.S. Appl. No. 15/380,419, filed Dec. 15, 2016.
U.S. Appl. No. 15/419,832, filed Jan. 30, 2017, 20170139017.
U.S. Appl. No. 15/400,794, filed Jan. 6, 2017, 20170115361.
U.S. Appl. No. 15/443,422, filed Feb. 27, 2017.
U.S. Appl. No. 15/437,222, filed Feb. 20, 2017, 20170120293.
U.S. Appl. No. 15/437,038, filed Feb. 20, 2017.
U.S. Appl. No. 15/440,194, filed Feb. 23, 2017.
U.S. Appl. No. 15/446,373, filed Mar. 1, 2017.
U.S. Appl. No. 15/450,504, filed Mar. 6, 2017.
U.S. Appl. No. 15/454,162, filed Mar. 9, 2017.
U.S. Appl. No. 15/456,913, filed Mar. 13, 2017.

(56) References Cited

OTHER PUBLICATIONS

U.S. Appl. No. 15/468,356, filed Mar. 24, 2017.
U.S. Appl. No. 15/468,397, filed Mar. 24, 2017.
U.S. Appl. No. 15/468,386, filed Mar. 24, 2017.
U.S. Appl. No. 15/468,289, filed Mar. 24, 2017.
U.S. Appl. No. 15/468,641, filed Mar. 24, 2017.
U.S. Appl. No. 15/468,582, filed Mar. 24, 2017.
U.S. Appl. No. 15/468,410, filed Mar. 24, 2017.
U.S. Appl. No. 15/468,951, filed Mar. 24, 2017.
U.S. Appl. No. 15/468,559, filed Mar. 24, 2017.
U.S. Appl. No. 15/468,282, filed Mar. 24, 2017.
U.S. Appl. No. 15/468,314, filed Mar. 24, 2017.
U.S. Appl. No. 15/468,274, filed Mar. 24, 2017.
U.S. Appl. No. 15/468,303, filed Mar. 24, 2017.
U.S. Appl. No. 15/469,374, filed Mar. 24, 2017.
U.S. Appl. No. 15/476,636, filed Mar. 31, 2017, 20170205526.
U.S. Appl. No. 15/479,256, filed Apr. 4, 2017, 20170207823.
U.S. Appl. No. 15/610,526, filed May 31, 2017.
U.S. Appl. No. 15/672,953, filed Aug. 9, 2017.
International Search Report and Written Opinion for PCT Appl. Ser. No. PCT/US2018/041411 dated Feb. 8, 2019, 13 pages.
Schonfeld, "Optical readout of single spins for quantum computing and magnetic sensing", Dissertation, Fachbereich Physlk der Freien Universitat Berlin, May 1, 2011, 21 Pages (relevant pages only), XP055143403. Retrieved from the Internet: URL: http://www.dIss.fu-berlIn.de/diss/servlets/MCRFIleNodeServIeUFU_DISS_derivate_00000001219_9/DIssertatIon_Slmon-choenfela_PublIcVersion-2.pdfJsessionid-89A943688E59.
US Final Office Action for U.S. Appl. No. 15/003,396 dated Mar. 22, 2019, 13 pages.
US Final Office Action for U.S. Appl. No. 15/382,045 dated Apr. 26, 2019, 16 pages.
US Final Office Action for U.S. Appl. No. 15/443,422 dated Mar. 7, 2019, 17 pages.
US Non-Final Office Action for U.S. Appl. No. 15/003,193 dated Apr. 11, 2019, 7 pages.
US Non-Final Office Action for U.S. Appl. No. 15/003,309 dated Feb. 13, 2019, 16 pages.
US Non-Final Office Action for U.S. Appl. No. 15/003,617 dated Feb. 26, 2019, 10 pages.
US Non-Final Office Action for U.S. Appl. No. 15/372,201 dated Apr. 2, 2019, 10 pages.
US Non-Final Office Action for U.S. Appl. No. 15/419,832 dated Feb. 8, 2019, 12 pages.
US Non-Final Office Action for U.S. Appl. No. 15/440,194 dated Feb. 15, 2019, 21 pages.
US Non-Final Office Action for U.S. Appl. No. 15/446,373 dated Apr. 19, 2019, 8 pages.
US Non-Final Office Action for U.S. Appl. No. 15/468,314 dated Mar. 28, 2019, 17 pages.
US Non-Final Office Action for U.S. Appl. No. 15/468,410 dated Apr. 11, 2019, 15 pages.
US Non-Final Office Action for U.S. Appl. No. 15/468,559 dated Apr. 11, 2019, 12 pages.
US Non-Final Office Action for U.S. Appl. No. 15/469,374 dated Feb. 28, 2019, 14 pages.
US Notice of Allowance for U.S. Appl. No. 15/003,617 dated Apr. 30, 2019, 9 pages.
US Notice of Allowance for U.S. Appl. No. 15/207,457 dated Mar. 6, 2019, 16 pages.
US Notice of Allowance for U.S. Appl. No. 15/376,244 dated Feb. 21, 2019, 7 pages.
US Notice of Allowance for U.S. Appl. No. 15/380,419 dated Feb. 26, 2019, 5 pages.
US Notice of Allowance for U.S. Appl. No. 15/400,794 dated Apr. 25, 2019, 5 pages.
US Notice of Allowance for U.S. Appl. No. 15/437,222 dated Mar. 25, 2019, 11 pages.
US Notice of Allowance for U.S. Appl. No. 15/468,282 dated Feb. 19, 2019, 8 pages.
US Notice of Allowance for U.S. Appl. No. 15/468,356 dated Apr. 22, 2019, 8 pages.
US Notice of Allowance for U.S. Appl. No. 15/468,582 dated Mar. 21, 2019, 13 pages.
US Notice of Allowance for U.S. Appl. No. 15/468,951 dated Mar. 28, 2019, 8 pages.

* cited by examiner

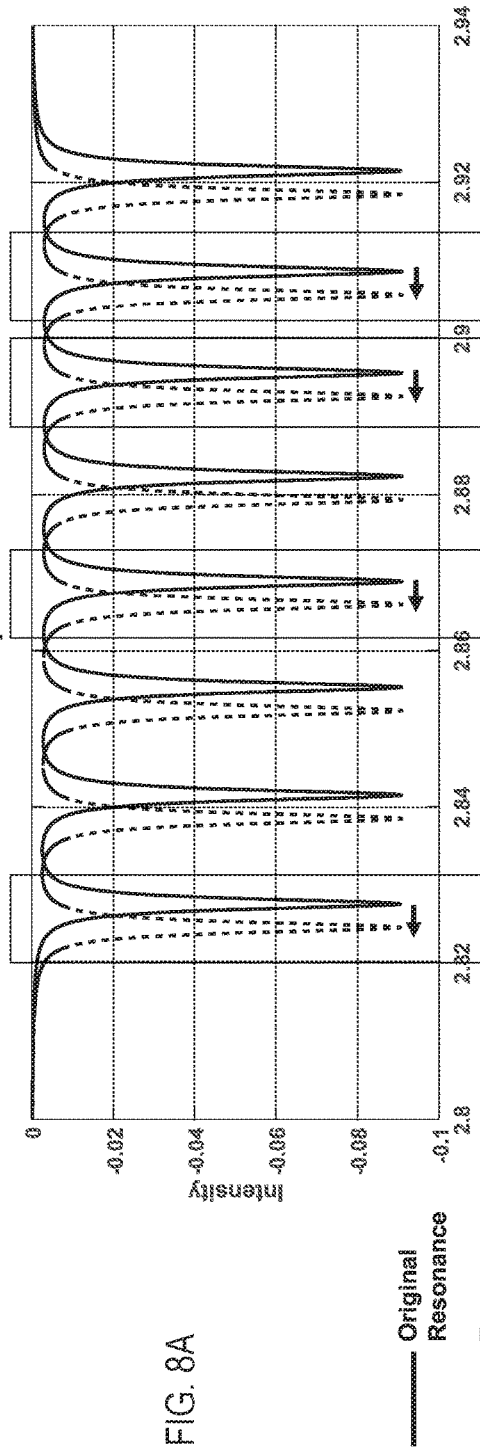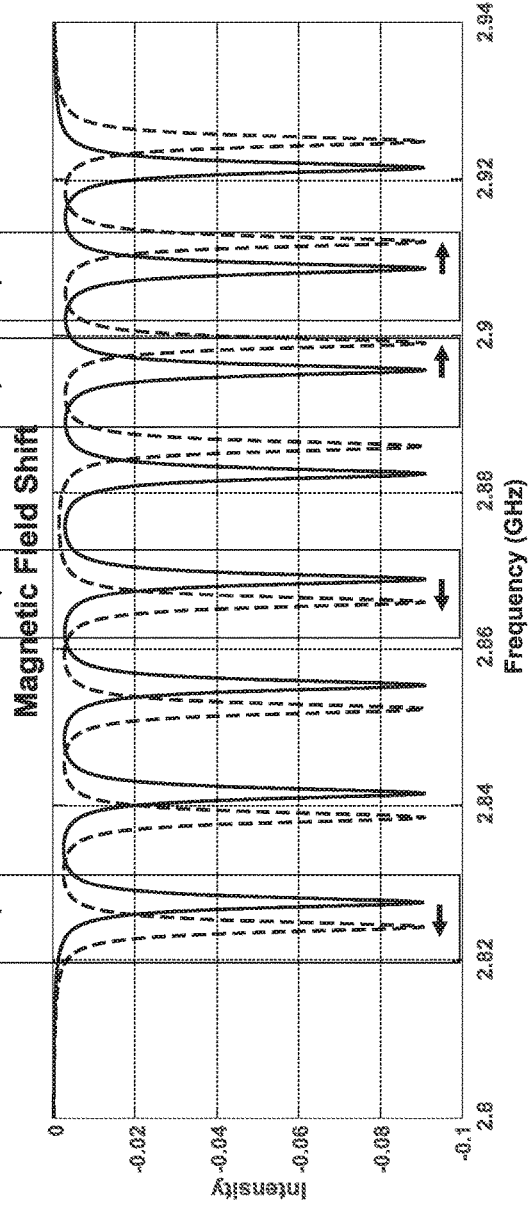
FIG. 8A
FIG. 8B

EFFICIENT THERMAL DRIFT COMPENSATION IN DNV VECTOR MAGNETOMETRY

FIELD

The present disclosure generally relates to magnetic detection systems, and more particularly, to measurement collection schemes for a magnetic detection system.

BACKGROUND

Many advanced magnetic detection (such as imaging) systems can operate in limited conditions, for example, high vacuum and/or cryogenic temperatures, which can make them inapplicable for applications that require ambient conditions. Small size, weight and power (SWAP) magnetic sensors of moderate sensitivity, vector accuracy, and bandwidth are likewise deficient for certain detection (such as imaging) applications.

SUMMARY

According to some embodiments, there is a system for magnetic detection of an external magnetic field, comprising: a nitrogen vacancy (NV) diamond material comprising a plurality of NV centers, the diamond material having a plurality of crystallographic axes each directed in different directions, the NV centers each corresponding to a respective one of the plurality of crystallographic axes; a radio frequency (RF) excitation source configured to provide RF excitations to the NV diamond material to excite electron spin resonances corresponding to the RF excitations, each crystallographic axis corresponding to a different electron spin resonance; an optical excitation source configured to provide optical excitation to the NV diamond material; an optical detector configured to receive an optical signal based on light emitted by the NV diamond material, the optical signal having a plurality of intensity changes corresponding respectively to electron spin resonances of the NV centers; and a controller configured to: receive a light detection signal from the optical detector based on the optical signal; determine the spectral position corresponding to some of the electron spin resonances based on the light detection signal; determine a measured four-dimensional projection of a magnetic field based on the determined spectral positions of a subset of all of the plurality of spin resonances, where the number of spin resonances in the subset is one half of a total number of the spin resonances; and determine an estimated three-dimensional magnetic field based on the measured four-dimensional magnetic field projections.

According to some embodiments, there are two different electron spin resonances for each of the crystallographic axes.

According to some embodiments, the total number of spin resonances is eight and the number of spin resonances in the subset of spin resonances is four.

According to some embodiments, the subset of spin resonances includes spin resonances corresponding to each of the crystallographic axes.

According to some embodiments, the controller is configured to determine the measured four-dimensional projected field based on a least squares fit.

According to some embodiments, spin resonances in the subset of spin resonances are selected to reduce thermal drift.

According to some embodiments, there is a system for magnetic detection of an external magnetic field, comprising: a magneto-optical defect center material comprising a plurality of magneto-optical defect centers, the magneto-optical defect center material having a plurality of crystallographic axes each directed in different directions, the magneto-optical defect centers each corresponding to a respective one of the plurality of crystallographic axes; a radio frequency (RF) excitation source configured to provide RF excitations to the magneto-optical defect center material to excite electron spin resonances corresponding to the RF excitations, each crystallographic axis corresponding to a different spin resonance; an optical excitation source configured to provide optical excitation to the magneto-optical defect center material; an optical detector configured to receive an optical signal based on light emitted by the magneto-optical defect center material, the optical signal having a plurality of intensity changes corresponding respectively to electron spin resonances of the magneto-optical defect centers; and a controller configured to: receive a light detection signal from the optical detector based on the optical signal; determine the spectral position corresponding to some of the electron spin resonances based on the light detection signal; determine a measured four-dimensional projection of a magnetic field based on the determined spectral positions of a subset of all of the plurality of spin resonances, where the number of spin resonances in the subset is one half of a total number of the spin resonances; and determine an estimated three-dimensional magnetic field based on the measured four-dimensional magnetic field projections.

According to some embodiments, the magneto-optical defect center material may comprise one of diamond, silicon carbide, or silicon.

According to some embodiments, there is a system for magnetic detection of an external magnetic field, comprising: a nitrogen vacancy (NV) diamond material comprising a plurality of NV centers, the diamond material having a plurality of crystallographic axes each directed in different directions, the NV centers each corresponding to a respective one of the plurality of crystallographic axes; a radio frequency (RF) excitation source configured to provide RF excitations to the NV diamond material to excite electron spin resonances corresponding to the RF excitations, each crystallographic axis corresponding to a different spin resonance; an optical excitation source configured to provide optical excitation to the NV diamond material; an optical detector configured to receive an optical signal based on light emitted by the NV diamond material, the optical signal having a plurality of intensity changes corresponding respectively to electron spin resonances of the NV centers; and a controller configured to: receive a light detection signal from the optical detector based on the optical signal; determine the spectral position corresponding to some of the electron spin resonances based on the light detection signal; determine a measured four-dimensional projection of a magnetic field based on some of the spectral positions of the plurality of spin resonances; determine an estimated three-dimensional magnetic field based on the measured four-dimensional magnetic field projection; and determine a shift in the estimated three-dimensional magnetic field due to thermal drift based on the estimated three-dimensional magnetic field and the measured four-dimensional magnetic field projection.

According to some embodiments, there is a method for determining an external magnetic field, comprising: applying RF excitations to nitrogen vacancy (NV) diamond material to excite electron spin resonances corresponding to the RF excitations, the NV diamond material comprising a plurality of NV centers, the NV diamond material having a plurality of crystallographic axes each directed in different directions, the NV centers each corresponding to a respective one of the plurality of crystallographic axes, each crystallographic axis corresponding to a different spin resonance; applying optical excitation to the NV diamond material; detecting an optical signal based on light emitted by the NV diamond material, the optical signal having a plurality of intensity changes corresponding respectively to electron spin resonances of the NV centers; receiving a light detection signal based on the detected optical signal; determining the spectral position corresponding to some of the electron spin resonances based on the light detection signal; determining a measured four-dimensional projection of a magnetic field based on the determined spectral positions of a subset of all of the plurality of spin resonances, where the number of spin resonances in the subset is one half of a total number of the spin resonances; and determining an estimated three-dimensional magnetic field based on the measured four-dimensional magnetic field projections.

According to some embodiments, there is a method for determining an external magnetic field, comprising: applying RF excitations to magneto-optical defect center material to excite electron spin resonances corresponding to the RF excitations, the magneto-optical defect center material comprising a plurality of magneto-optical defect centers, the magneto-optical defect center material having a plurality of crystallographic axes each directed in different directions, the magneto-optical defect centers each corresponding to a respective one of the plurality of crystallographic axes, each crystallographic axis corresponding to a different spin resonance; applying optical excitation to the magneto-optical defect center material; detecting an optical signal based on light emitted by the magneto-optical defect center material, the optical signal having a plurality of intensity changes corresponding respectively to electron spin resonances of the magneto-optical defect centers; receiving a light detection signal based on the detected optical signal; determining the spectral position corresponding to some of the electron spin resonances based on the light detection signal; determining a measured four-dimensional projection of a magnetic field based on the determined spectral positions of a subset of all of the plurality of spin resonances, where the number of spin resonances in the subset is one half of a total number of the spin resonances; and determining an estimated three-dimensional magnetic field based on the measured four-dimensional magnetic field projections.

According to some embodiments, there is a method for determining an external magnetic field, comprising: applying RF excitations to nitrogen vacancy (NV) diamond material to excite electron spin resonances corresponding to the RF excitations, the NV diamond material comprising a plurality of NV centers, the NV diamond material having a plurality of crystallographic axes each directed in different directions, the NV centers each corresponding to a respective one of the plurality of crystallographic axes, each crystallographic axis corresponding to a different spin resonance; applying optical excitation to the NV diamond material; detecting an optical signal based on light emitted by the NV diamond material, the optical signal having a plurality of intensity changes corresponding respectively to electron spin resonances of the NV centers; receiving a light detection signal based on the detected optical signal; determining the spectral position corresponding to some of the electron spin resonances based on the light detection signal; determining a measured four-dimensional projection of a magnetic field based on some of the spectral positions of the plurality of spin resonances; determining an estimated three-dimensional magnetic field based on the measured four-dimensional magnetic field projections; and determining a shift in the estimated three-dimensional magnetic field due to thermal drift based on the estimated three-dimensional magnetic field and the measured four-dimensional magnetic field projections.

According to some embodiments, there is a method for determining an external magnetic field, comprising: applying RF excitations to magneto-optical defect center material to excite electron spin resonances corresponding to the RF excitations, the magneto-optical defect center material comprising a plurality of magneto-optical defect centers, the magneto-optical defect center material having a plurality of crystallographic axes each directed in different directions, the magneto-optical defect centers each corresponding to a respective one of the plurality of crystallographic axes, each crystallographic axis corresponding to a different spin resonance; applying optical excitation to the magneto-optical defect center material; detecting an optical signal based on light emitted by the magneto-optical defect center material, the optical signal having a plurality of intensity changes corresponding respectively to electron spin resonances of the magneto-optical defect centers; receiving a light detection signal based on the detected optical signal; determining the spectral position corresponding to some of the electron spin resonances based on the light detection signal; determining a measured four-dimensional projection of a magnetic field based on some of the spectral positions of the plurality of spin resonances; determining an estimated three-dimensional magnetic field based on the measured four-dimensional magnetic field projections; and determining a shift in the estimated three-dimensional magnetic field due to thermal drift based on the estimated three-dimensional magnetic field and the measured four-dimensional magnetic field projections.

BRIEF DESCRIPTION OF THE DRAWINGS

FIG. 8A is a graph illustrating two fluorescence curves as a function of RF frequency for two different temperatures where electron spin resonances 1, 4, 6 and 7 are selected in the case where the external magnetic field is aligned with the bias magnetic field.

FIG. 8B is a graph illustrating two fluorescence curves as a function of RF frequency for two different magnetic fields where electron spin resonances 1, 4, 6 and 7 are selected in the case where the external magnetic field is aligned with the bias magnetic field.

DETAILED DESCRIPTION

The present disclosure relates to systems and methods for estimating a full three-dimensional magnetic field from a magneto-optical defect center material, such as a NV center diamond material. The systems and methods only require using the spectral position of four electron spin resonances to recover a full three-dimensional estimated magnetic field, in the case of NV diamond material. By using only a subset of the full eight electron spin resonances, a faster vector sampling rate is possible.

Further the systems and methods described for determining the estimated three-dimensional magnetic field are insensitive to temperature drift. Thus, the temperature drift is inherently accounted for.

Still further, according to the systems and methods described, the thermal drift in the spectral position of the electron spin resonances used in the magnetic field estimation may be readily calculated based on a four-dimensional measured projected magnetic field (onto the diamond lattice vectors) and the three-dimensional estimated magnetic field.

The NV Center, its Electronic Structure, and Optical and RF Interaction

Figure 1:
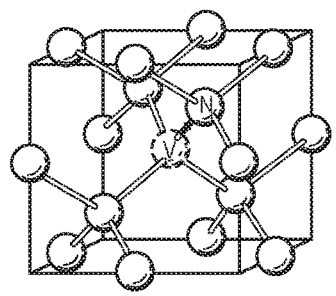
FIG. 1 illustrates one orientation of a nitrogen vacancy (NV) center in a diamond lattice.

The NV center in a diamond comprises a substitutional nitrogen atom in a lattice site adjacent a carbon vacancy as shown in FIG. 1. The NV center may have four orientations, each corresponding to a different crystallographic axis of the diamond lattice.

The NV center may exist in a neutral charge state or a negative charge state. The neutral charge state uses the nomenclature $NV^0$, while the negative charge state uses the nomenclature NV.

The NV center has a number of electrons, including three unpaired electrons, each one from the vacancy to a respective of the three carbon atoms adjacent to the vacancy, and a pair of electrons between the nitrogen and the vacancy. The NV center, which is in the negatively charged state, also includes an extra electron.

Figure 2:
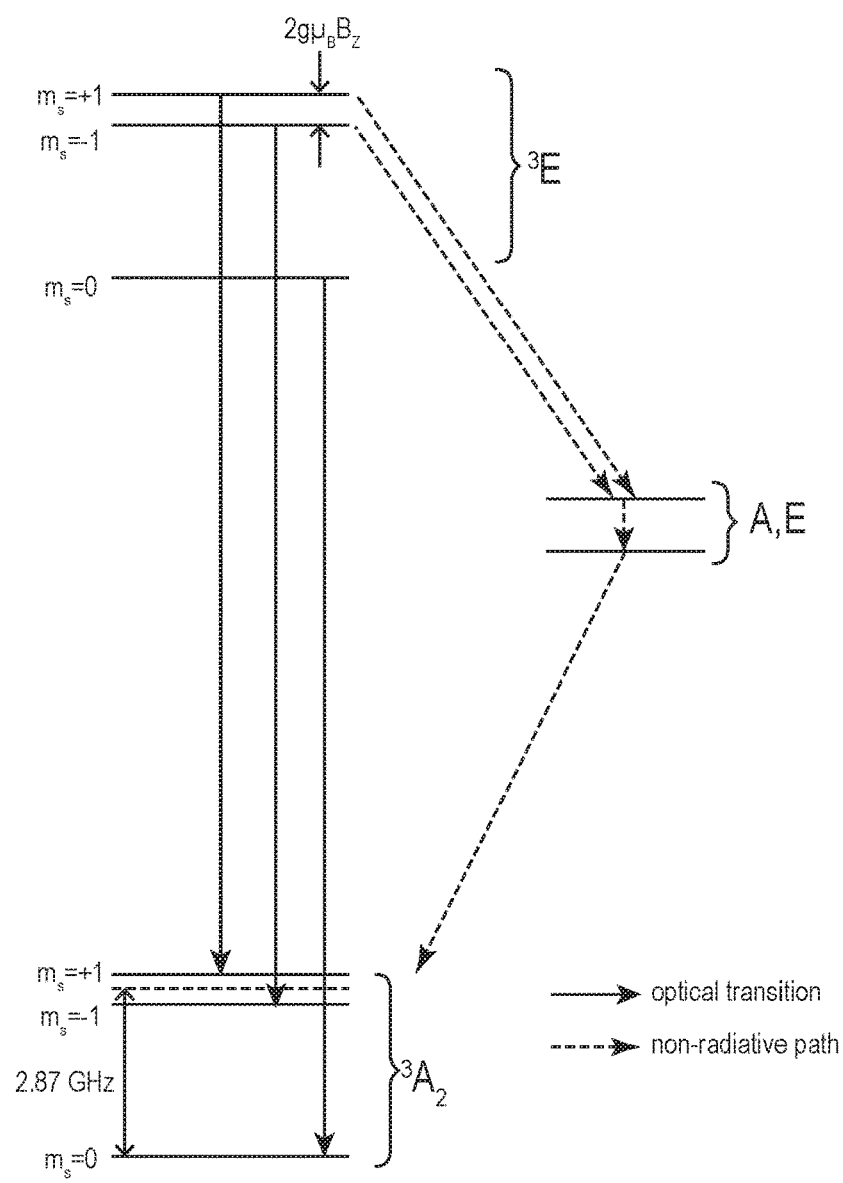
FIG. 2 is an energy level diagram showing energy levels of spin states for an NV center.

The NV center has rotational symmetry, and as shown in FIG. 2, has a ground state, which is a spin triplet with $^3A_2$ symmetry with one spin state $m_s=0$, and two further spin states $m_s=+1$, and $m_s=-1$. In the absence of an external magnetic field, the $m_s=\pm 1$ energy levels are offset from the $m_s=0$ due to spin-spin interactions, and the $m_s=\pm 1$ energy levels are degenerate, i.e., they have the same energy. The $m_s=0$ spin state energy level is split from the $m_s=\pm 1$ energy levels by an energy of 2.87 GHz for a zero external magnetic field.

Introducing an external magnetic field with a component along the NV axis lifts the degeneracy of the $m_s=\pm 1$ energy levels, splitting the energy levels $m_s=\pm 1$ by an amount $2g\mu_B Bz$, where g is the g-factor, $\mu_B$ is the Bohr magneton, and Bz is the component of the external magnetic field along the NV axis. This relationship is correct to a first order and inclusion of higher order corrections is a straightforward matter and will not materially affect the computational and logic steps.

The NV center electronic structure further includes an excited triplet state $^3E$ with corresponding $m_s=0$ and $m_s=\pm 1$ spin states. The optical transitions between the ground state $^3A_2$ and the excited triplet $^3E$ are predominantly spin conserving, meaning that the optical transitions are between initial and final states that have the same spin. For a direct transition between the excited triplet $^3E$ and the ground state $^3A_2$, a photon of red light is emitted with a photon energy corresponding to the energy difference between the energy levels of the transitions.

An alternative non-radiative decay route from the triplet $^3E$ to the ground state $^3A_2$ via intermediate electron states exists, in which the intermediate states are thought to be intermediate singlet states A, E with intermediate energy levels. The transition rate from the $m_s=\pm 1$ spin states of the excited triplet $^3E$ to the intermediate energy levels is significantly greater than the transition rate from the $m_s=0$ spin state of the excited triplet $^3E$ to the intermediate energy levels. The transition from the singlet states A, E to the ground state triplet $^3A_2$ predominantly decays to the $m_s=0$ spin state over the $m_s=\pm 1$ spins states. These features of the decay from the excited triplet $^3E$ state via the intermediate singlet states A, E to the ground state triplet $^3A_2$ allows that, if optical excitation is provided to the system, the optical excitation will eventually pump the NV center into the $m_s=0$ spin state of the ground state $^3A_2$. In this way, the population of the $m_s=0$ spin state of the ground state $^3A_2$ may be reset to a maximum polarization determined by the decay rates from the triplet $^3E$ to the intermediate singlet states.

Another feature of the decay is that the fluorescence intensity due to optically stimulating the excited triplet $^3E$ state is less for the $m_s=\pm 1$ states than for the $m_s=0$ spin state. This is so because the decay via the intermediate states does not result in a photon emitted in the fluorescence band, and because of the greater probability that the $m_s=\pm 1$ states of the excited triplet $^3E$ state will decay via the non-radiative decay path. The lower fluorescence intensity for the $m_s=\pm 1$ states than for the $m_s=0$ spin state allows the fluorescence intensity to be used to determine the spin state. As the population of the $m_s=\pm 1$ states increases relative to the $m_s=0$ spin, the overall fluorescence intensity will be reduced.

The NV Center, or Magneto-Optical Defect Center, Magnetic Sensor System

Figure 3:
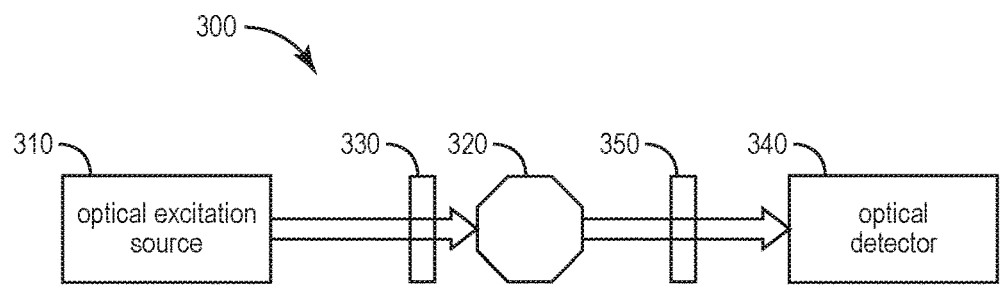
FIG. 3 is a schematic diagram illustrating an NV center magnetic sensor system.

FIG. 3 is a schematic diagram illustrating an NV center magnetic sensor system 300 that uses fluorescence intensity to distinguish the $m_s=\pm 1$ states, and to measure the magnetic field based on the energy difference between the $m_s=+1$ state and the $m_s=-1$ state. The system 300 includes an optical excitation source 310, which directs optical excitation to an NV diamond material 320 with NV centers. The system further includes an RF excitation source 330, which provides RF radiation to the NV diamond material 320. Light from the NV diamond may be directed through an optical filter 350 to an optical detector 340.

The RF excitation source 330 may be a microwave coil, for example. The RF excitation source 330, when emitting RF radiation with a photon energy resonant with the transition energy between ground $m_s=0$ spin state and the $m_s=+1$ spin state, excites a transition between those spin states. For such a resonance, the spin state cycles between ground $m_s=0$ spin state and the $m_s=+1$ spin state, reducing the population in the $m_s=0$ spin state and reducing the overall fluorescence at resonances. Similarly, resonance occurs between the $m_s=0$ spin state and the $m_s=-1$ spin state of the ground state when the photon energy of the RF radiation emitted by the RF excitation source is the difference in energies of the $m_s=0$ spin state and the $m_s=-1$ spin state, or between the $m_s=0$ spin state and the $m_s=+1$ spin state, there is a decrease in the fluorescence intensity.

The optical excitation source 310 may be a laser or a light emitting diode, for example, which emits light in the green, for example. The optical excitation source 310 induces fluorescence in the red, which corresponds to an electron transition from the excited state to the ground state. Light from the NV diamond material 320 is directed through the optical filter 350 to filter out light in the excitation band (in the green, for example), and to pass light in the red fluorescence band, which in turn is detected by the detector 340. The optical excitation light source 310, in addition to exciting fluorescence in the diamond material 320, also serves to reset the population of the $m_s=0$ spin state of the ground state $^3A_2$ to a maximum polarization, or other desired polarization.

Figure 4:
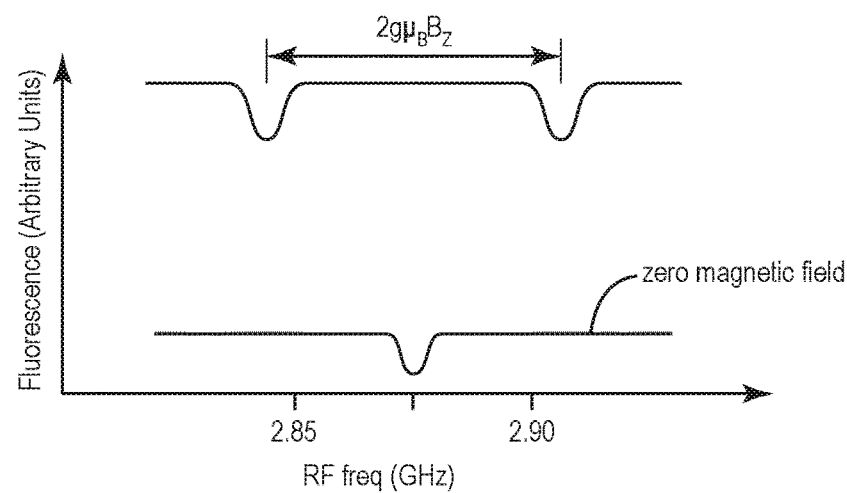
FIG. 4 is a graph illustrating the fluorescence as a function of an applied RF frequency of an NV center along a given direction for a zero magnetic field.

For continuous wave excitation, the optical excitation source 310 continuously pumps the NV centers, and the RF excitation source 330 sweeps across a frequency range that includes the zero splitting (when the $m_s=\pm 1$ spin states have the same energy) photon energy of 2.87 GHz. The fluorescence for an RF sweep corresponding to a diamond material 320 with NV centers aligned along a single direction is shown in FIG. 4 for different magnetic field components Bz along the NV axis, where the energy splitting between the $m_s=-1$ spin state and the $m_s=+1$ spin state increases with Bz. Thus, the component Bz may be determined. Optical excitation schemes other than continuous wave excitation are contemplated, such as excitation schemes involving pulsed optical excitation, and pulsed RF excitation. Examples of pulsed excitation schemes include Ramsey pulse sequence and spin echo pulse sequence.

Figure 5B:
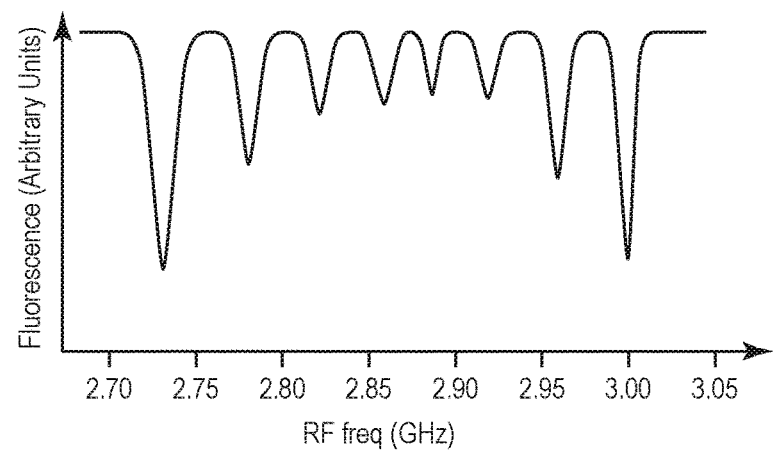
FIG. 5B is a graph illustrating the fluorescence as a function of an applied RF frequency for four different NV center orientations for a non-zero magnetic field.
Figure 5A:
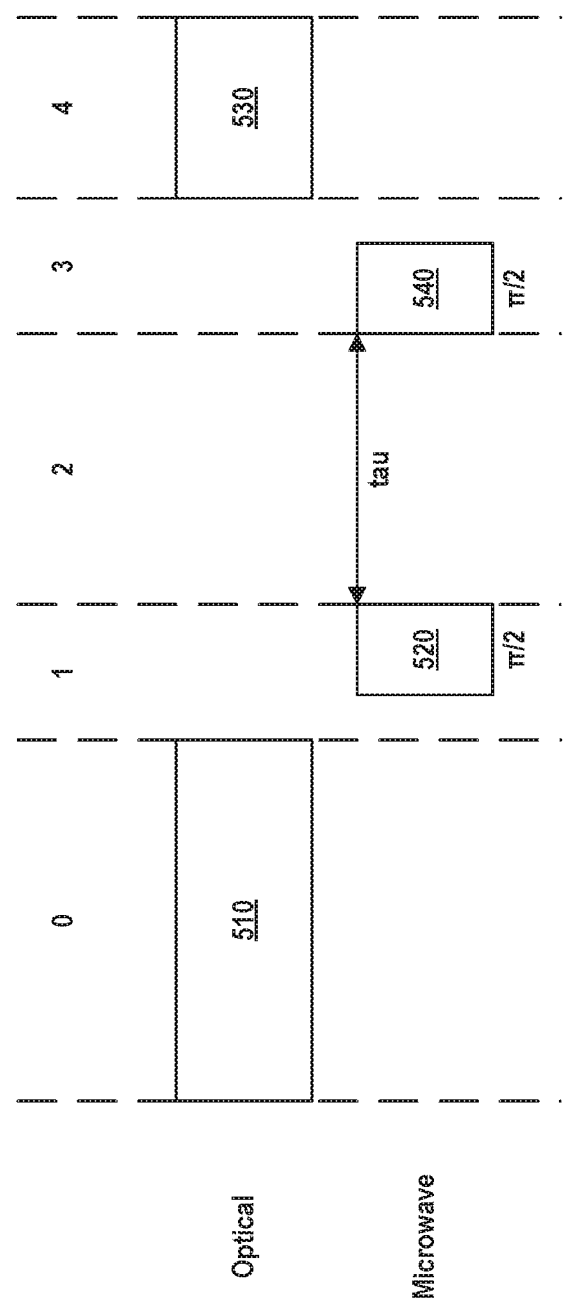
FIG. 5A is a schematic illustrating a Ramsey sequence of optical excitation pulses and RF excitation pulses.

The Ramsey pulse sequence is a pulsed RF-pulsed laser scheme that measures the free precession of the magnetic moment in the diamond material 320 with NV centers, and is a technique that quantum mechanically prepares and samples the electron spin state. FIG. 5A is a schematic diagram illustrating the Ramsey pulse sequence. As shown in FIG. 5A, a Ramsey pulse sequence includes optical excitation pulses and RF excitation pulses over a five-step period. In a first step, during a period 0, a first optical excitation pulse 510 is applied to the system to optically pump electrons into the ground state (i.e., $m_s=0$ spin state). This is followed by a first RF excitation pulse 520 (in the form of, for example, a microwave (MW) $\pi/2$ pulse) during a period 1. The first RF excitation pulse 520 sets the system into superposition of the $m_s=0$ and $m_s=+1$ spin states (or, alternatively, the $m_s=0$ and $m_s=-1$ spin states, depending on the choice of resonance location). During a period 2, the system is allowed to freely precess (and dephase) over a time period referred to as tau ($\tau$). During this free precession time period, the system measures the local magnetic field and serves as a coherent integration. Next, a second RF excitation pulse 540 (in the form of, for example, a MW $\pi/2$ pulse) is applied during a period 3 to project the system back to the $m_s=0$ and $m_s=+1$ basis. Finally, during a period 4, a second optical pulse 530 is applied to optically sample the system and a measurement basis is obtained by detecting the fluorescence intensity of the system. The RF excitation pulses applied are provided at a given RF frequency, which correspond to a given NV center orientation.

In general, the diamond material 320 will have NV centers aligned along directions of four different orientation classes, and thus along the four different crystallographic axes of diamond. FIG. 5B illustrates a response curve, specifically fluorescence, as a function of RF frequency for the case where the diamond material 320 has NV centers aligned along directions of four different orientation classes. In this case, the component Bz along each of the different orientations may be determined. FIG. 5B illustrates a spectra with eight electron spin resonances, with two electron spin resonances for each diamond crystallographic axis, the two electron spin resonances corresponding to the $m_s=-1$ spin state and the $m_s=+1$ spin state. The electron spin resonances are positioned on the FIG. 5B spectra at spectral positions along the RF frequency axis of FIG. 5. In FIG. 5B the eight electron spin resonances are separated to be at different spectral positions along the RF frequency axis.

While FIG. 3 illustrates an NV center magnetic sensor system 300 with NV diamond material 320 with a plurality of NV centers, in general, the magnetic sensor system may instead employ a different magneto-optical defect center material, with a plurality of magneto-optical defect centers. The electron spin state energies of the magneto-optical defect centers shift with magnetic field, and the optical response, such as fluorescence, for the different spin states is not the same for all of the different spin states. In this way, the magnetic field may be determined based on optical excitation, and possibly RF excitation, in a corresponding way to that described above with NV diamond material. The magneto-optical defect centers may be spin centers in silicon carbide, for example, where the substrate may be formed of silicon carbide, or the defect centers may be atomic substitutions in silicon, such as phosphorous in silicon, for example. In general, the electron spin centers may be in magneto-optical defect center material.

Figure 6:
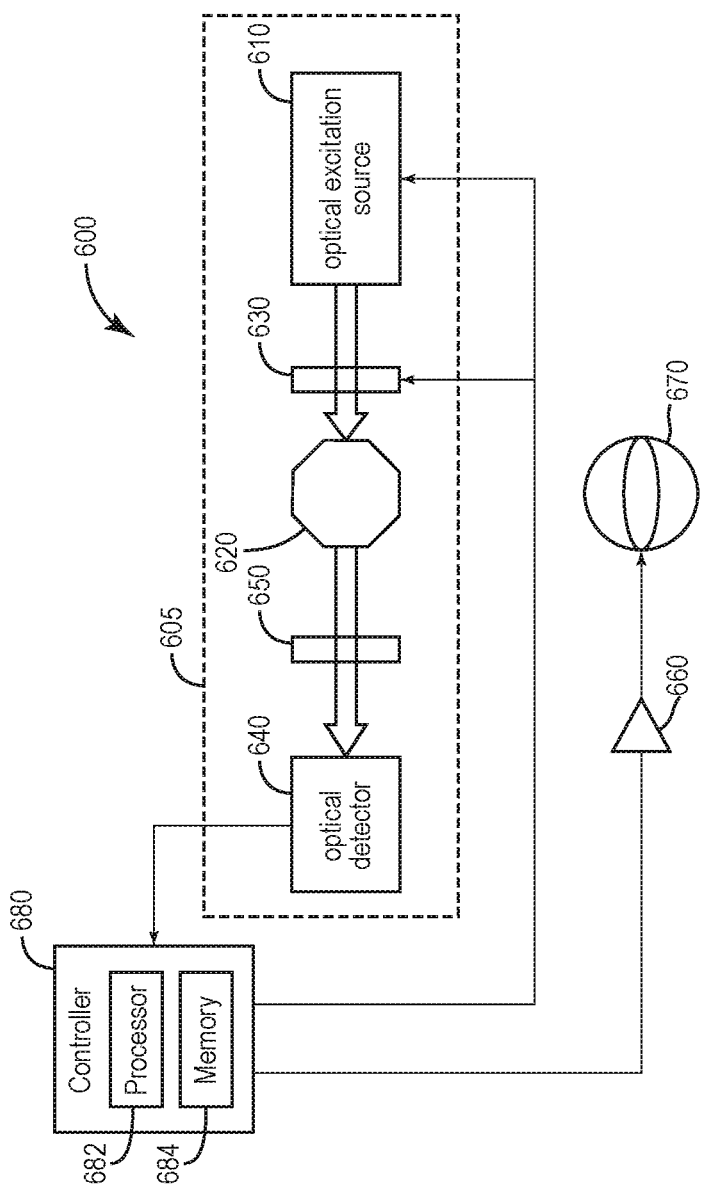
FIG. 6 is a schematic diagram illustrating some embodiments of a magnetic field detection system.

FIG. 6 is a schematic diagram of a system 600 for a magnetic field detection system according to some embodiments. The system 600 includes an optical excitation source 610, which directs optical excitation to an NV diamond material 620 with NV centers, or another magneto-optical defect center material with magneto-optical defect centers. An RF excitation source 630 provides RF radiation to the NV diamond material 620. A magnetic field generator 670 generates a magnetic field, which is detected at the NV diamond material 620.

The magnetic field generator 670 may generate magnetic fields with orthogonal polarizations, for example. In this regard, the magnetic field generator 670 may include two or more magnetic field generators, such as two or more Helmholtz coils or other magnetic electronic devices. The two or more magnetic field generators may be configured to provide a magnetic field having a predetermined direction, each of which provide a relatively uniform magnetic field at the NV diamond material 620. The predetermined directions may be orthogonal to one another. In addition, the two or more magnetic field generators of the magnetic field generator 670 may be disposed at the same position, or may be separated from each other. In the case that the two or more magnetic field generators are separated from each other, the two or more magnetic field generators may be arranged in an array, such as a one-dimensional or two-dimensional array, for example.

The system 600 may be arranged to include one or more optical detection systems 605, where each of the optical detection systems 605 includes the optical detector 640, optical excitation source 610, and NV diamond material 620. Furthermore, the magnetic field generator 670 may have a relatively high power as compared to the optical detection systems 605. In this way, the optical systems 605 may be deployed in an environment that requires a relatively lower power for the optical systems 605, while the magnetic field generator 670 may be deployed in an environment that has a relatively high power available for the magnetic field generator 670 so as to apply a relatively strong magnetic field.

The system 600 further includes a controller 680 arranged to receive a light detection signal from the optical detector 640 and to control the optical excitation source 610, the RF excitation source 630, and the second magnetic field generator 675, and to perform calculations. The controller may be a single controller, or multiple controllers. For a controller including multiple controllers, each of the controllers may perform different functions, such as controlling different components of the system 600. The second magnetic field generator 675 may be controlled by the controller 680 via an amplifier 660, for example.

The RF excitation source 630 may be a microwave coil, for example. The RF excitation source 630 is controlled to emit RF radiation with a photon energy resonant with the transition energy between the ground $m_s=0$ spin state and the $m_s=\pm 1$ spin states as discussed above with respect to FIG. 3.

The optical excitation source 610 may be a laser or a light emitting diode, for example, which emits light in the green, for example. The optical excitation source 610 induces fluorescence in the red from the NV diamond material 620, where the fluorescence corresponds to an electron transition from the excited state to the ground state. Light from the NV diamond material 620 is directed through the optical filter 650 to filter out light in the excitation band (in the green, for example), and to pass light in the red fluorescence band, which in turn is detected by the optical detector 640. The optical excitation light source 610, in addition to exciting fluorescence in the NV diamond material 620, also serves to reset the population of the $m_s=0$ spin state of the ground state $^3A_2$ to a maximum polarization, or other desired polarization.

The controller 680 is arranged to receive a light detection signal from the optical detector 640 and to control the optical excitation source 610, the RF excitation source 630, and the second magnetic field generator 675. The controller may include a processor 682 and a memory 684, in order to control the operation of the optical excitation source 610, the RF excitation source 630, and the second magnetic field generator 675, and to perform calculations. The memory 684, which may include a nontransitory computer readable medium, may store instructions to allow the operation of the optical excitation source 610, the RF excitation source 630, and the second magnetic field generator 675 to be controlled. That is, the controller 680 may be programmed to provide control.

Measurement Collection Process

According to certain embodiments, the controller 680 controls the operation of the optical excitation source 610, the RF excitation source 630, and the magnetic field generator 670 to perform Optically Detected Magnetic Resonance (ODMR). Specifically, the magnetic field generator 670 may be used to apply a bias magnetic field that sufficiently separates the intensity responses corresponding to electron spin resonances for each of the four NV center orientations. The controller 680 then controls the optical excitation source 610 to provide optical excitation to the NV diamond material 620 and the RF excitation source 630 to provide RF excitation to the NV diamond material 620. The resulting fluorescence intensity responses for each of the NV axes are collected over time to determine the components of the external magnetic field Bz aligned along directions of the four NV center orientations which respectively correspond to the four diamond lattice crystallographic axes of the NV diamond material 620, which may then be used to calculate the estimated vector magnetic field acting on the system 600. The excitation scheme utilized during the measurement collection process (i.e., the applied optical excitation and the applied RF excitation) may be any appropriate excitation scheme. For example, the excitation scheme may utilize continuous wave (CW) magnetometry, pulsed magnetometry, and variations on CW and pulsed magnetometry (e.g., pulsed RF excitation with CW optical excitation). In cases where Ramsey pulse RF sequences are used, pulse parameters π and τ may be optimized using Rabi analysis and FID-Tau sweeps prior to the collection process, as described in, for example, U.S. patent application Ser. No. 15/003,590.

During the measurement collection process, fluctuations may occur in the measured intensity response due to effects caused by components of the system 600, rather than due to true changes in the external magnetic field. For example, prolonged optical excitation of the NV diamond material by the optical excitation source 610 may cause vertical (e.g., red photoluminescence intensity) fluctuations, or vertical drift, in the intensity response, causing the response curve to shift upward or downward over time. In addition, thermal effects within the system 600 may result in horizontal (e.g., frequency) fluctuations, or horizontal drift, in the measured intensity response, causing the response curve to shift left or right over time depending on whether the temperature of the magneto-optical defect center material has increased or decreased.

Axes of the NV Centers

In deriving the three-dimensinal magnetic field vector impinging on the system 600 from the measurements obtained by the intensity response produced by the NV diamond material 620, it is desirable to establish the orientation of the NV defect center axes, or magneto-optical defect center axes more broadly, of the NV diamond material 620, or the magneto-optical defect center material more broadly, to allow for the accurate recovery of the magnetic field vector and maximize signal-to-noise information. Since the NV defect center axes are aligned along the respective crystallographic axes of the diamond lattice for the NV diamond material 620, the analysis below is with respect to the four crystallographic axes of the diamond lattice. Of course, the number of crystallographic axes will depend upon the material used in general for the magneto-optical defect center material, and may be a different number than four.

Figure 7:
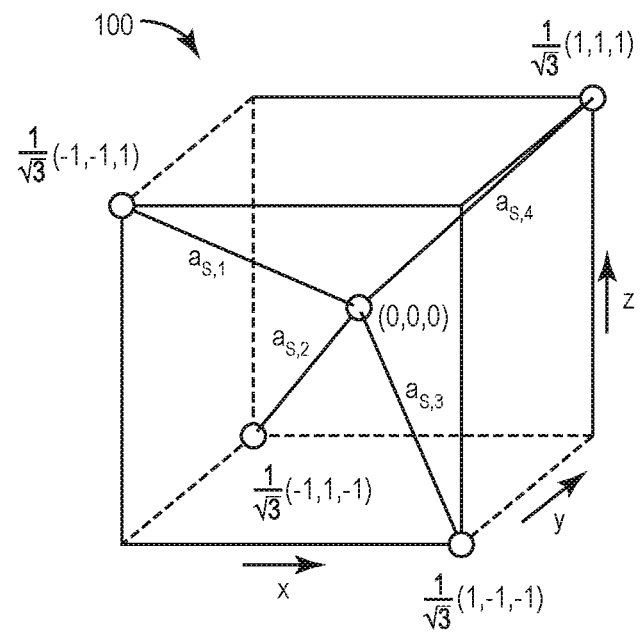
FIG. 7 is a unit cell diagram of the crystal structure of a diamond lattice having a standard orientation.

As shown in FIG. 7, a Cartesian reference frame having {x, y, z} orthogonal axes may be used, but any arbitrary reference frame and orientation may be used. FIG. 7 shows a unit cell 100 of a diamond lattice having a "standard" orientation. In practice, the diamond lattice of the NV diamond material may be rotated relative to the standard orientation, but the rotation may be accounted for, for example, as discussed in U.S. application Ser. No. 15/003,718 entitled "APPARATUS AND METHOD FOR RECOVERY OF THREE DIMENSIONAL MAGNETIC FIELD FROM A MAGNETIC DETECTION SYSTEM", filed Jan. 21, 2016, the entire contents of which are incorporated herein. For simplicity, only the standard orientation will be discussed here. The axes of the diamond lattice will fall along four possible directions. Thus, the four axes in a standard orientation may be defined as unit vectors corresponding to:

$$a_{S,1} = \frac{1}{\sqrt{3}}[-1 \quad -1 \quad 1]^T \quad (1)$$

$$a_{S,2} = \frac{1}{\sqrt{3}}[-1 \quad 1 \quad -1]^T$$

$$a_{S,3} = \frac{1}{\sqrt{3}}[1 \quad -1 \quad -1]^T$$

$$a_{S,4} = \frac{1}{\sqrt{3}}[1 \quad 1 \quad 1]^T$$

For simplicity, the four vectors of equation (1) may be represented by a single matrix $A_S$, which represents the standard orientation of the unit cell 100:

$$A_S = [a_{S,1} \quad a_{S,2} \quad a_{S,3} \quad a_{S,4}] = \frac{1}{\sqrt{3}}\begin{bmatrix} -1 & -1 & 1 & 1 \\ -1 & 1 & -1 & 1 \\ 1 & -1 & -1 & 1 \end{bmatrix} \quad (2)$$

Model for No Temperature Shift

Assuming the response is linear with the magnetic field, the true magnetic field b may be expressed as a linear model on the four coordinate axes as:

$$A^T b + w = m \quad (3)$$

where: $b \in \mathbb{R}^{3 \times 1}$ is the true magnetic field vector in the NV diamond material excluding any field produced by a permanent magnet bias; $w \in \mathbb{R}^{4 \times 1}$ is a sensor noise vector; $m \in \mathbb{R}^{4 \times 1}$ is a vector where the $i^{th}$ element represents the magnetic field measurements along the $i^{th}$ axis; and $A^T b$ gives the projection of the true magnetic field vector onto each of the four axes and $A^T$ is the transpose of $A_S$. More generally, $A^T$ represents the orientation of the diamond lattice after an arbitrary orthonormal rotation and possible reflection of the axes matrix $A_S$.

The bias magnetic field serves to separate the Lorentzians response curves of the fluorescence measurement corresponding to the electron spin resonances associated with the different crystallographic axes of the diamond material. For two spin states $m_s = \pm 1$ for each crystallographic axis, there will be 8 Lorentzians, two Lorentzians corresponding to each crystallographic axis. The bias magnetic field may be calibrated to separate the Lorentzians corresponding to the different electron spin resonances as described in U.S. application Ser. No. 15/003,718 entitled "APPARATUS AND METHOD FOR RECOVERY OF THREE DIMENSIONAL MAGNETIC FIELD FROM A MAGNETIC DETECTION SYSTEM."

Further, for a given crystallographic axis and its corresponding two spin states, the magnitude of the projection of the magnetic field along the crystallographic axis can be determined, but the sign or direction of the projection will not be initially unknown. The sign due to the bias magnetic field for each crystallographic axis can also be recovered as described in U.S. application Ser. No. 15/003,718 entitled "APPARATUS AND METHOD FOR RECOVERY OF THREE DIMENSIONAL MAGNETIC FIELD FROM A MAGNETIC DETECTION SYSTEM."

Model with Temperature Shift

The model from equation 3 can be expanded to include temperature drift as follows, where it is presumed that the measurements of the different electron spin resonances are taken simultaneously or at least quickly enough that the temperature drift between measurements is insignificant.

$$A^T b + c + w = m \quad (4)$$

where $c \in$ $$\mathbb{R}^{4 \times 1} = \begin{bmatrix} c \\ c \\ c \\ c \end{bmatrix} \quad 5$$

is a constant vector representing a fixed, but unknown offset c on the measurements from all four axes due to temperature. This model is valid presuming the sign used during the sign recovery process, due to the bias magnetic field, is the same for all four electron spin resonances, used. Such uniformity in the per lattice sign recovery process ensures that the modeled scalar translations of each lattice due to thermal drift share the same sign and, thus, that the drift vector represents a constant vector rather than a vector whose elements have fixed magnitude but varying sign. For a true quad bias magnet configuration (e.g., an alignment in which the bias magnet projects onto the lattice vectors in a relative 7:5:3:1 ratio), potential sets of valid resonances, where the resonances are denoted as 1-8 starting from the left, would be {1, 4, 6, 7} or {2, 3, 5, 8}, for example. This is shown below.

FIG. 8A illustrates two fluorescence curves as a function of RF frequency for two different temperatures in the case the external magnetic field is aligned with the bias magnetic field. Each of the fluorescence curves has eight electron spin resonances, each electron spin resonance corresponding to one crystallographic axis and one spin state. Each of the resonances shifts in the same direction due to a temperature shift for those resonances where the sign used during the sign recovery process, due to the bias magnetic field, is the same. In this case, resonances in the set {1, 4, 6, 7} shift in the same direction based on temperature shift.

FIG. 8B illustrates two fluorescence curves as a function of RF frequency for two different magnetic fields based on a change in the bias magnetic field. In this case, the external magnetic field is aligned with the bias magnetic field and creates an equal shift in each lattice with comparable amplitude to the thermal shift in FIG. 8A. Each of the fluorescence curves has eight resonances, each resonance corresponding to one crystallographic axis and one spin state. As can be seen, the resonance shifts need not all shift in the same direction based on a magnetic field shift for the set of resonances {1, 4, 6, 7}.

Figure 8C:
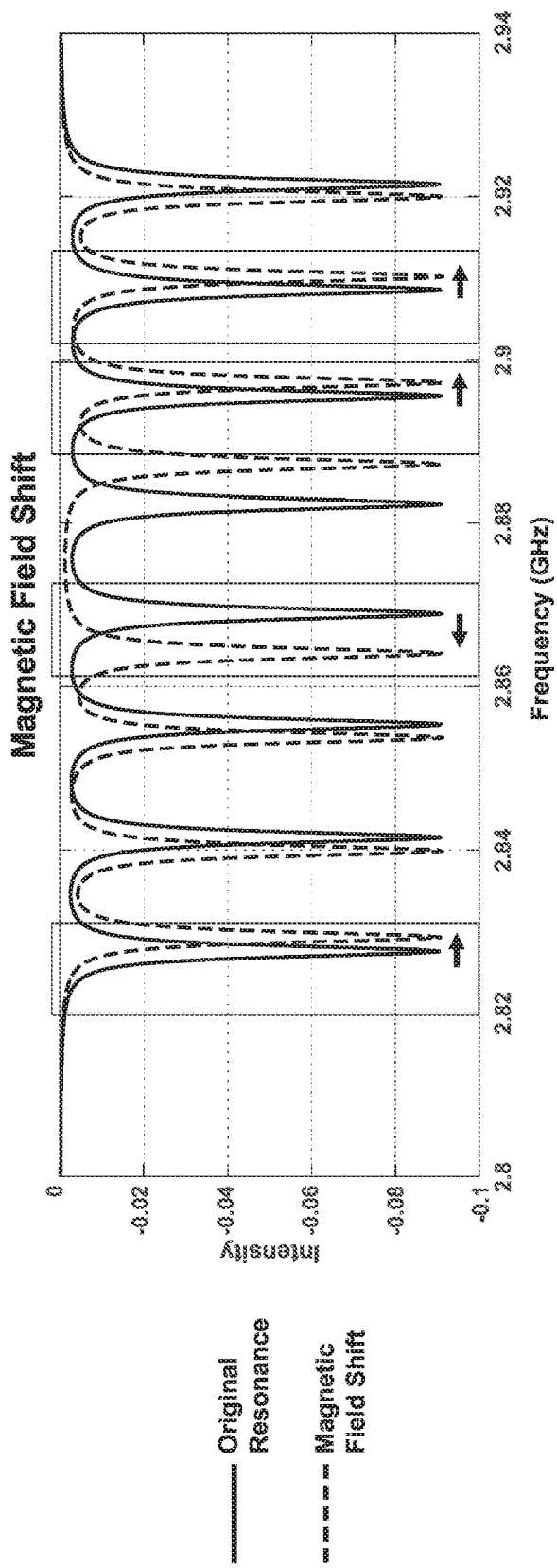
FIG. 8C is a graph illustrating two fluorescence curves as a function of RF frequency for two different magnetic fields where electron spin resonances 1, 4, 6 and 7 are selected in the case of a general external magnetic field.

FIG. 8C is similar to FIG. 8B but shows the resonances need not all shift in the same direction and with the same amplitude based on a magnetic field shift for the set of resonances {1, 4, 6, 7} in the case of a more general external field. In FIGS. 8A-8C, the results are based on a continuous wave measurement.

Temperature Insensitive Solution to Estimated Magnetic Field

The magnetic field may now be determined using only a subset of all of the eight resonances, namely four of the eight resonances. Given the linear model for magnetic field measurement, a least-squares solution for the total magnetic field $\hat{b}$ acting on the system based on the four measurements (using sets {1, 4, 6, 7} or {2, 3, 5, 8}) in the absence of temperature drift may be provided as:

$$\hat{b} = (A^T)^+ m = \frac{3}{4} A m = \frac{3}{4} A(A^T b + w) = b + \frac{3}{4} A w = b + w' \quad (5)$$

where $$w' = \frac{3}{4}Aw$$

represents a scaled sensor noise vector, $A^T$ is the transpose of A, and the subscript+denotes the pseudoinverse. Applying this solution to the model with a temperature drift provides equation (6) below:

$$\hat{b} = (A^T)^+ m = \frac{3}{4}Am$$

$$= \frac{3}{4}A(A^T b + c + w)$$

$$= b + \frac{3}{4}Ac + \frac{3}{4}Aw$$

$$= b + \frac{3}{4}\frac{1}{\sqrt{3}}\begin{bmatrix} -1 & -1 & 1 & 1 \\ -1 & 1 & -1 & 1 \\ 1 & -1 & -1 & 1 \end{bmatrix} c + w'$$

$$= b + \frac{3}{4}\frac{1}{\sqrt{3}}\begin{bmatrix} 0 \\ 0 \\ 0 \\ 0 \end{bmatrix} + w'$$

$$= b + w'$$

Thus, the temperature drift term c disappears from the least-squares solution and the solution is therefore insensitive to temperature drift. Moreover, only a subset of all of the resonances need be used to determine the three-dimensional magnetic field.

Estimation of Thermal Drift

The thermal drift term c may be determined based on the estimated three-dimensional magnetic field $\hat{b}$ acting on the DNV material. In particular, an estimate of the offset c vector and, hence, the scalar constant of the thermal offset, c, which is the per element magnitude, can be obtained by projecting the estimated three-dimensional magnetic field $\hat{b}$ back onto the four lattice vectors and differencing this projection with the original magnetic field measurements m as follows in equation (7):

$$m - A^T \hat{b} = (A^T b + c + w) - A^T(b + w') =$$

$$(A^T b + c + w) - \left(A^T b + A^T \frac{3}{4}Aw\right) = c + w - \frac{3}{4}A^T Aw = c + w - w = c$$

Thus, the thermal offset due to temperature drift may be calculated based on the four-dimensional magnetic field measurements m and the estimated three-dimensional magnetic field $\hat{b}$, which is projected onto the crystallographic axes.

The present disclosure relates to systems and methods for estimating a full three-dimensional magnetic field from a magneto-optical defect center material, such as a NV center material. The systems and methods only require using the spectral position of four electron spin resonances to recover a full three-dimensional estimated magnetic field, in the case of NV diamond material. By using only a subset of the full eight electron spin resonances, a faster thermally-compensated vector sampling rate is possible.

Further the systems and methods described for determining the estimated three-dimensional magnetic field are insensitive to temperature drift. Thus, the temperature drift is inherently accounted for.

Still further, according to the systems and methods described, the thermal drift in the spectral position of the electron spin resonances used in the magnetic field estimation may be readily calculated based on the four-dimensional measured magnetic field lattice projections and the three-dimensional estimated magnetic field.

Embodiments have been described in detail with particular reference to preferred embodiments, but it will be understood by those skilled in the art that variations and modifications can be effected within the spirit and scope of this disclosure.

What is claimed is:

1. A system for magnetic detection of an external magnetic field, comprising:
   a nitrogen vacancy (NV) diamond material comprising a plurality of NV centers, the diamond material having a plurality of crystallographic axes each directed in different directions, the NV centers each corresponding to a respective one of the plurality of crystallographic axes;
   a radio frequency (RF) excitation source configured to provide RF excitations to the NV diamond material to excite electron spin resonances corresponding to the RF excitations, each crystallographic axis corresponding to a different electron spin resonance;
   an optical excitation source configured to provide optical excitation to the NV diamond material;
   an optical detector configured to receive an optical signal based on light emitted by the NV diamond material, the optical signal having a plurality of intensity changes corresponding respectively to electron spin resonances of the NV centers; and
   a controller configured to:
   receive a light detection signal from the optical detector based on the optical signal;
   determine the spectral position corresponding to some of the electron spin resonances based on the light detection signal;
   determine a measured four-dimensional projection of a magnetic field based on the determined spectral positions of a subset of all of the plurality of spin resonances, where the number of spin resonances in the subset is one half of a total number of the spin resonances; and
   determine an estimated three-dimensional magnetic field based on the measured four-dimensional magnetic field projections.

2. The system of claim 1 where there are two different electron spin resonances for each of the crystallographic axes.

3. The system of claim 2, wherein the total number of spin resonances is eight and the number of spin resonances in the subset of spin resonances is four.

4. The system of claim 3, wherein the subset of spin resonances includes spin resonances corresponding to each of the crystallographic axes.

5. The system of claim 3, wherein the controller is configured to determine the measured four-dimensional projected field based on a least squares fit.

6. The system of claim 2, wherein spin resonances in the subset of spin resonances are selected to reduce thermal drift.

7. A system for magnetic detection of an external magnetic field, comprising:
   a magneto-optical defect center material comprising a plurality of magneto-optical defect centers, the mag neto-optical defect center material having a plurality of crystallographic axes each directed in different directions, the magneto-optical defect centers each corresponding to a respective one of the plurality of crystallographic axes;

a radio frequency (RF) excitation source configured to provide RF excitations to the magneto-optical defect center material to excite electron spin resonances corresponding to the RF excitations, each crystallographic axis corresponding to a different spin resonance;

an optical excitation source configured to provide optical excitation to the magneto-optical defect center material;

an optical detector configured to receive an optical signal based on light emitted by the magneto-optical defect center material, the optical signal having a plurality of intensity changes corresponding respectively to electron spin resonances of the magneto-optical defect centers; and a controller configured to:

receive a light detection signal from the optical detector based on the optical signal;

determine the spectral position corresponding to some of the electron spin resonances based on the light detection signal;

determine a measured four-dimensional projection of a magnetic field based on the determined spectral positions of a subset of all of the plurality of spin resonances, where the number of spin resonances in the subset is one half of a total number of the spin resonances; and determine an estimated three-dimensional magnetic field based on the measured four-dimensional magnetic field projections.

8. The system of claim 7 where there are two different electron spin resonances for each of the crystallographic axes.

9. The system of claim 8, wherein the total number of spin resonances is eight and the number of spin resonances in the subset of spin resonances is four.

10. The system of claim 9, wherein the subset of spin resonances includes spin resonances corresponding to each of the crystallographic axes.

11. The system of claim 9, wherein the controller is configured to determine the measured four-dimensional field based on a least squares fit.

12. The system of claim 8, wherein spin resonances in the subset of spin resonances are selected to reduce thermal drift.

13. The system of claim 7 where the magneto-optical defect center material may comprise one of diamond, silicon carbide, or silicon.

14. A system for magnetic detection of an external magnetic field, comprising:

a nitrogen vacancy (NV) diamond material comprising a plurality of NV centers, the diamond material having a plurality of crystallographic axes each directed in different directions, the NV centers each corresponding to a respective one of the plurality of crystallographic axes;

a radio frequency (RF) excitation source configured to provide RF excitations to the NV diamond material to excite electron spin resonances corresponding to the RF excitations, each crystallographic axis corresponding to a different spin resonance;

an optical excitation source configured to provide optical excitation to the NV diamond material;

an optical detector configured to receive an optical signal based on light emitted by the NV diamond material, the optical signal having a plurality of intensity changes corresponding respectively to electron spin resonances of the NV centers; and a controller configured to:

receive a light detection signal from the optical detector based on the optical signal;

determine the spectral position corresponding to some of the electron spin resonances based on the light detection signal;

determine a measured four-dimensional projection of a magnetic field based on some of the spectral positions of the plurality of spin resonances;

determine an estimated three-dimensional magnetic field based on the measured four-dimensional magnetic field projection; and determine a shift in the estimated three-dimensional magnetic field due to thermal drift based on the estimated three-dimensional magnetic field and the measured four-dimensional magnetic field projection.

15. The system of claim 14 where there are two different electron spin resonances for each of the crystallographic axes.

16. The system of claim 3, wherein the controller is configured to determine the measured four-dimensional projected field based on a least squares fit.

17. A method for determining an external magnetic field, comprising:

applying RF excitations to nitrogen vacancy (NV) diamond material to excite electron spin resonances corresponding to the RF excitations, the NV diamond material comprising a plurality of NV centers, the NV diamond material having a plurality of crystallographic axes each directed in different directions, the NV centers each corresponding to a respective one of the plurality of crystallographic axes, each crystallographic axis corresponding to a different spin resonance;

applying optical excitation to the NV diamond material;

detecting an optical signal based on light emitted by the NV diamond material, the optical signal having a plurality of intensity changes corresponding respectively to electron spin resonances of the NV centers;

receiving a light detection signal based on the detected optical signal;

determining the spectral position corresponding to some of the electron spin resonances based on the light detection signal;

determining a measured four-dimensional projection of a magnetic field based on the determined spectral positions of a subset of all of the plurality of spin resonances, where the number of spin resonances in the subset is one half of a total number of the spin resonances; and determining an estimated three-dimensional magnetic field based on the measured four-dimensional magnetic field projections.

18. The method of claim 17 where there are two different electron spin resonances for each of the crystallographic axes.

19. The method of claim 18, wherein the total number of spin resonances is eight and the number of spin resonances in the subset of spin resonances is four.

20. The method of claim 19, wherein the subset of spin resonances includes spin resonances corresponding to each of the crystallographic axes.

21. The method of claim 19, wherein the measured four-dimensional projected field is based on a least squares fit.

22. The method of claim 18, wherein spin resonances in the subset of spin resonances are selected to reduce thermal drift.

23. A method for determining an external magnetic field, comprising:
applying RF excitations to magneto-optical defect center material to excite electron spin resonances corresponding to the RF excitations, the magneto-optical defect center material comprising a plurality of magneto-optical defect centers, the magneto-optical defect center material having a plurality of crystallographic axes each directed in different directions, the magneto-optical defect centers each corresponding to a respective one of the plurality of crystallographic axes, each crystallographic axis corresponding to a different spin resonance;
applying optical excitation to the magneto-optical defect center material;
detecting an optical signal based on light emitted by the magneto-optical defect center material, the optical signal having a plurality of intensity changes corresponding respectively to electron spin resonances of the magneto-optical defect centers;
receiving a light detection signal based on the detected optical signal;
determining the spectral position corresponding to some of the electron spin resonances based on the light detection signal;
determining a measured four-dimensional projection of a magnetic field based on the determined spectral positions of a subset of all of the plurality of spin resonances, where the number of spin resonances in the subset is one half of a total number of the spin resonances; and
determining an estimated three-dimensional magnetic field based on the measured four-dimensional magnetic field projections.

24. The method of claim 23 where the magneto-optical defect center material may comprise one of diamond, silicon carbide, or silicon.

25. A method for determining an external magnetic field, comprising:
applying RF excitations to nitrogen vacancy (NV) diamond material to excite electron spin resonances corresponding to the RF excitations, the NV diamond material comprising a plurality of NV centers, the NV diamond material having a plurality of crystallographic axes each directed in different directions, the NV centers each corresponding to a respective one of the plurality of crystallographic axes, each crystallographic axis corresponding to a different spin resonance;
applying optical excitation to the NV diamond material;
detecting an optical signal based on light emitted by the NV diamond material, the optical signal having a plurality of intensity changes corresponding respectively to electron spin resonances of the NV centers;
receiving a light detection signal based on the detected optical signal;
determining the spectral position corresponding to some of the electron spin resonances based on the light detection signal;
determining a measured four-dimensional projection of a magnetic field based on some of the spectral positions of the plurality of spin resonances;
determining an estimated three-dimensional magnetic field based on the measured four-dimensional magnetic field projections; and
determining a shift in the estimated three-dimensional magnetic field due to thermal drift based on the estimated three-dimensional magnetic field and the measured four-dimensional magnetic field projections.

26. The method of claim 25, wherein the determining the measured multi-dimensional field is based on a least squares fit.

27. A method for determining an external magnetic field, comprising:
applying RF excitations to magneto-optical defect center material to excite electron spin resonances corresponding to the RF excitations, the magneto-optical defect center material comprising a plurality of magneto-optical defect centers, the magneto-optical defect center material having a plurality of crystallographic axes each directed in different directions, the magneto-optical defect centers each corresponding to a respective one of the plurality of crystallographic axes, each crystallographic axis corresponding to a different spin resonance;
applying optical excitation to the magneto-optical defect center material;
detecting an optical signal based on light emitted by the magneto-optical defect center material, the optical signal having a plurality of intensity changes corresponding respectively to electron spin resonances of the magneto-optical defect centers;
receiving a light detection signal based on the detected optical signal;
determining the spectral position corresponding to some of the electron spin resonances based on the light detection signal;
determining a measured four-dimensional projection of a magnetic field based on some of the spectral positions of the plurality of spin resonances;
determining an estimated three-dimensional magnetic field based on the measured four-dimensional magnetic field projections; and
determining a shift in the estimated three-dimensional magnetic field due to thermal drift based on the estimated three-dimensional magnetic field and the measured four-dimensional magnetic field projections.

28. The method of claim 27, wherein where the magneto-optical defect center material may comprise one of diamond, silicon carbide, or silicon.

* * * * *